US012721881B2

(12) United States Patent
Feghali-Bostwick

(10) Patent No.: US 12,721,881 B2
(45) Date of Patent: Sep. 1, 2026

(54) ENDOSTATIN PEPTIDES FOR THE TREATMENT OF TUMORS, FIBROSIS AND ACUTE LUNG INJURY

(71) Applicant: MUSC Foundation for Research Development, Charleston, SC (US)

(72) Inventor: Carol Feghali-Bostwick, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 16/919,680

(22) Filed: Jul. 2, 2020

(65) Prior Publication Data

US 2021/0008173 A1 Jan. 14, 2021

Related U.S. Application Data

(60) Provisional application No. 62/872,301, filed on Jul. 10, 2019.

(51) Int. Cl.

| | |
|---|---|
| ***A61K 38/00*** | (2006.01) |
| ***A61K 38/08*** | (2019.01) |
| ***A61K 38/10*** | (2006.01) |
| ***A61K 38/39*** | (2006.01) |
| ***A61P 11/00*** | (2006.01) |
| ***A61P 35/00*** | (2006.01) |

(52) U.S. Cl.

CPC .............. *A61K 38/39* (2013.01); *A61K 38/08* (2013.01); *A61K 38/10* (2013.01); *A61P 11/00* (2018.01); *A61P 35/00* (2018.01)

(58) Field of Classification Search

CPC ........ A61K 38/39; A61K 38/10; A61K 38/08; A61P 35/00; A61P 11/00

See application file for complete search history.

(56) References Cited

U.S. PATENT DOCUMENTS

| | | | | |
|---|---|---|---|---|
| 5,854,205 A | 12/1998 | O'Reilly | | |
| 6,174,861 B1 | 1/2001 | O'Reilly | | |
| 6,306,819 B1 | 10/2001 | Rupnick | | |
| 6,346,510 B1 | 2/2002 | O'Reilly | | |
| 6,630,448 B2 | 10/2003 | O'Reilly | | |
| 6,764,995 B2 | 7/2004 | O'Reilly | | |
| 6,921,749 B1 | 7/2005 | Chillemi | | |
| 7,495,089 B2 | 2/2009 | O'Reilly | | |
| 7,524,811 B2 * | 4/2009 | Folkman | C07K 14/78 | 514/1.1 |
| 7,645,735 B2 | 1/2010 | Folkman | | |
| 7,655,458 B2 | 2/2010 | O'Reilly | | |
| 8,507,441 B2 * | 8/2013 | Feghali-Bostwick | A61K 38/39 | 514/18.6 |
| 8,716,232 B2 * | 5/2014 | Feghali-Bostwick | A61K 38/08 | 514/18.6 |
| 9,365,616 B2 * | 6/2016 | Feghali-Bostwick | C07K 7/06 | |
| 9,556,252 B2 * | 1/2017 | Feghali-Bostwick | A61K 38/08 | |
| 10,172,923 B2 * | 1/2019 | Feghali-Bostwick | A61K 38/39 | |
| 10,709,769 B2 * | 7/2020 | Feghali-Bostwick | C07K 14/47 | |
| 2002/0127595 A1 | 9/2002 | O'Reilly | | |
| 2003/0082228 A1 | 5/2003 | Flowers | | |
| 2003/0114370 A1 | 6/2003 | Folkman | | |
| 2003/0219426 A1 | 11/2003 | O'Reilly | | |
| 2004/0073007 A1 | 4/2004 | Chillemi | | |
| 2009/0280190 A1 | 11/2009 | Folkman | | |
| 2014/0194365 A1 | 7/2014 | Feghali-Bostwick | | |
| 2017/0210823 A1 | 7/2017 | Sagi | | |
| 2018/0179263 A1 | 6/2018 | Feghali-Bostwick | | |
| 2019/0142956 A1 | 5/2019 | Tomasini-Johansson | | |

FOREIGN PATENT DOCUMENTS

| | | |
|---|---|---|
| EP | 1024801 B1 | 6/2004 |
| EP | 1268783 B1 | 6/2006 |
| EP | 1668129 B1 | 10/2008 |
| WO | 1999048924 A1 | 9/1999 |
| WO | 2001034174 A2 | 5/2001 |

OTHER PUBLICATIONS

Samuel et al. Anti-fibrotic actions of relaxin, British Journal of Pharmacology, 2017, 962-976 (Year: 2017).*

Kulke et al. "Phase II Study of Recombinant Human Endostating in Patients With Advanced Neuroendocrine Tumors", Journal of Clinical Oncology, 2006, 3555-3561 (Year: 2006).*

Chillemi et al. "Studies on the Structure-Activity Relationship of Endostatin: Synthesis of Human Endostatin Peptides Exhibiting Potent Antiangiogenic Activities", J. Med. Chem, 2003, 4165-4172 (Year: 2003).*

Sengupta_et_al_Nucleic_Acids_Res_Nov. 2, 2018_vol. 46_No. 19_pp. 9932-9950 (Year: 2018).*

Slansky_et_al_Semin_Immunol_Feb. 2020_vol. 47_epub_Mar. 20, 2020 (Year: 2020).*

Abdollahi A, Hahnfeldt P, Maercker C, et al. Endostatin's antiangiogenic signaling network. Mol Cell. 2004;13(5):649-663.

Cattaneo MG, Pola S, Francescato P, Chillemi F, Vicentini LM. Human endostatin-derived synthetic peptides possess potent antiangiogenic properties in vitro and in vivo. Exp Cell Res. 2003;283(2):230-236.

Chillemi F, Francescato P, Ragg E, Cattaneo MG, Pola S, Vicentini L. Studies on the structure-activity relationship of endostatin: synthesis of human endostatin peptides exhibiting potent antiangiogenic activities. J Med Chem. Sep. 11, 2003;46(19):4165-72.

Dhanabal M, Ramchandran R, Volk R, et al. Endostatin: yeast production, mutants, and antitumor effect in renal cell carcinoma. Cancer Res. 1999;59(1):189-197.

Ding YH, Javaherian K, Lo KM, et al. Zinc-dependent dimers observed in crystals of human endostatin. Proc Natl Acad Sci U S A. 1998;95(18):10443-10448.

(Continued)

*Primary Examiner* — Catherine S Hibbert
(74) *Attorney, Agent, or Firm* — Riverside Law LLP

(57) ABSTRACT

The present invention provides compositions and methods for treatment or prevention of tumor growth, fibrosis, acute lung injury or a combination thereof. In one embodiment, the composition comprises a peptide derived from the C-terminal region of endostatin.

18 Claims, 32 Drawing Sheets

Specification includes a Sequence Listing.

(56) References Cited

OTHER PUBLICATIONS

Folkman J, Kalluri R. Tumor Angiogenesis. In: Kufe DW, Pollock RE, Weichselbaum RR, et al., editors. Holland-Frei Cancer Medicine. 6th edition. Hamilton (ON): Bc Decker; 2003. Chapter 11.
Hajitou A, Grignet C, Devy L, et al. The antitumoral effect of endostatin and angiostatin is associated with a down-regulation of vascular endothelial growth factor expression in tumor cells. FASEB J. 2002;16(13):1802-1804.
Hanai J, Dhanabal M, Karumanchi SA, et al. Endostatin causes G1 arrest of endothelial cells through inhibition of cyclin D1. J Biol Chem. 2002;277(19):16464-16469.
Hohenester E, Sasaki T, Olsen BR, Timpl R. Crystal structure of the angiogenesis inhibitor endostatin at 1.5 A resolution. EMBO J. 1998;17(6):1656-1664.
Javaherian K, Park SY, Pickl WF, et al. Laminin modulates morphogenic properties of the collagen XVIII endostatin domain. J Biol Chem. 2002;277(47):45211-45218.
Karumanchi SA, Jha V, Ramchandran R, et al. Cell surface glypicans are low-affinity endostatin receptors. Mol Cell. 2001;7(4):811-822.
Kim YM, Hwang S, Kim YM, et al. Endostatin blocks vascular endothelial growth factor-mediated signaling via direct interaction with KDR/Flk-1. J Biol Chem. 2002;277(31):27872-27879.
Kim YM, Jang JW, Lee OH, et al. Endostatin inhibits endothelial and tumor cellular invasion by blocking the activation and catalytic activity of matrix metalloproteinase. Cancer Res. 2000;60(19):5410-5413.
Kisker O, Becker CM, Prox D, et al. Continuous administration of endostatin by intraperitoneally implanted osmotic pump improves the efficacy and potency of therapy in a mouse xenograft tumor model. Cancer Res. 2001;61(20):7669-7674.
Lee SJ, Jang JW, Kim YM, et al. Endostatin binds to the catalytic domain of matrix metalloproteinase-2. FEBS Lett. 2002;519(1-3):147-152.
Liu G, Lu S, Wang X, et al. Perturbation of NK cell peripheral homeostasis accelerates prostate carcinoma metastasis. J Clin Invest. 2013;123(10):4410-4422.
Morbidelli L, Donnini S, Chillemi F, Giachetti A, Ziche M. Angiosuppressive and angiostimulatory effects exerted by synthetic partial sequences of endostatin. Clin Cancer Res. Nov. 1, 2003;9(14):5358-69.
Nyberg P, Heikkila P, Sorsa T, et al. Endostatin inhibits human tongue carcinoma cell invasion and intravasation and blocks the activation of matrix metalloprotease-2, -9, and -13. J Biol Chem. 2003;278(25):22404-22411.
O'Reilly MS, Boehm T, Shing Y, et al. Endostatin: an endogenous inhibitor of angiogenesis and tumor growth. Cell. 1997;88(2):277-285.
Sasaki T, Larsson H, Kreuger J, et al. Structural basis and potential role of heparin/heparan sulfate binding to the angiogenesis inhibitor endostatin. EMBO J. 1999;18(22):6240-6248.
Shichiri M, Hirata Y. Antiangiogenesis signals by endostatin. FASEB J. 2001;15(6):1044-1053.
Takahashi K, Saishin Y, Saishin Y, et al. Intraocular expression of endostatin reduces VEGF-induced retinal vascular permeability, neovascularization, and retinal detachment. FASEB J. 2003;17(8):896-898.
Wickström SA, Alitalo K, Keski-Oja J. Endostatin associates with integrin alpha5beta1 and caveolin-1, and activates Src via a tyrosyl phosphatase-dependent pathway in human endothelial cells. Cancer Res. 2002;62(19):5580-5589.
Wickström SA, Alitalo K, Keski-Oja J. Endostatin associates with lipid rafts and induces reorganization of the actin cytoskeleton via down-regulation of RhoA activity. J Biol Chem. 2003;278(39):37895-37901.
Xu HL, Tan HN, Wang FS, Tang W. Research advances of endostatin and its short internal fragments. Curr Protein Pept Sci. Jun. 2008;9(3):275-83.
Yamaguchi Y, Takihara T, Chambers RA, Veraldi KL, Larregina AT, Feghali-Bostwick CA. A peptide derived from endostatin ameliorates organ fibrosis. Sci Transl Med. May 30, 2012;4(136):136ra71.
Yoon SS, Eto H, Lin CM, et al. Mouse endostatin inhibits the formation of lung and liver metastases. Cancer Res. 1999;59(24):6251-6256.
Kozono, S., et al., "Pirfenidone Inhibits Pancreatic Cancer Desmoplasia by Regulating Stellate Cells," Tumor and Stem Cell Biology, vol. 73, No. 7 (2013), pp. 2345-2356.
Wan, Y.-Y., et al., "Endostatin, an angiogenesis inhibitor, ameliorates bleomycin-induced pulmonary fibrosis in rats," Respiratory Research, vol. 14 (2013), Article 56.

* cited by examiner

Figure 1

| Treatments | Day | N | Mean | Std Dev | Minimum | Maximum |
|---|---|---|---|---|---|---|
| BioE4 | 0 | 5 | 154.1 | 12.7 | 140.6 | 173.1 |
| | 2 | 5 | 241.9 | 106.9 | 152.1 | 410.1 |
| | 5 | 5 | 307.5 | 105.0 | 188.2 | 429.9 |
| | 7 | 4 | 359.7 | 133.7 | 184.0 | 499.4 |
| | 9 | 4 | 482.9 | 234.9 | 252.4 | 807.9 |
| | 11 | 4 | 703.1 | 383.6 | 384.7 | 1259.4 |
| | 13 | 4 | 786.3 | 412.0 | 407.1 | 1285.3 |
| | 15 | 4 | 902.0 | 418.0 | 422.5 | 1347.3 |
| Control | 0 | 4 | 154.8 | 17.9 | 140.3 | 179.3 |
| | 2 | 4 | 221.5 | 39.9 | 178.4 | 272.9 |
| | 5 | 4 | 278.4 | 21.2 | 257.0 | 307.6 |
| | 7 | 4 | 595.9 | 96.7 | 458.7 | 684.3 |
| | 9 | 4 | 730.0 | 184.2 | 571.5 | 994.4 |
| | 11 | 4 | 875.8 | 117.3 | 708.6 | 970.3 |
| | 13 | 4 | 1162.6 | 184.9 | 950.3 | 1331.3 |
| | 15 | 4 | 1464.1 | 27.1 | 1425.6 | 1488.0 |

Figure 3

| Effect | Estimate | Standard Error | DF | t Value | Pr > \|t\| |
|---|---|---|---|---|---|
| **Intercept** | 153.58 | 97.7400 | 7 | 1.57 | 0.1601 |
| **Day** | 18.4949 | 23.5118 | 54 | 0.79 | 0.4349 |
| **Day*Day** | 4.5909 | 1.4558 | 54 | 3.15 | 0.0026 |
| **BioE4** | 0.8204 | 131.15 | 7 | 0.01 | 0.9952 |
| **Day x BioE4** | 6.1624 | 32.0055 | 54 | 0.19 | 0.8480 |
| **$Day^2$ x BioE4** | -2.9196 | 1.9987 | 54 | -1.46 | 0.1499 |

Figure 4

| | | | |
|---|---|---|---|
| | **Model-Based Estimate of Mean Volume on Day 15** | **Standard Error** | **95% Confidence Interval for the Mean** |
| | | | |
| | | | |
| **Control Group** | 1464.0 $mm^3$ | 97.7 | (1268.0, 1659.9) |
| **BioE4 Group** | 900.3 $mm^3$ | 97.4 | (705.1, 1095.6) |
| | | | |
| **Difference (Control – BioE4)** | 563.7 $mm^3$ | 138.0 | (287.0, 840.3) |
| | | | |
| | | | |
| | **Model-Based Estimate of Mean Rate of Increase in Volume on Day 15** | **Standard Error** | **95% Confidence Interval for the Mean** |
| | | | |
| | | | |
| **Control Group** | 156.2 $mm^3$ per day | 23.5 | (109.0, 203.4) |
| **BioE4 Group** | 74.8 $mm^3$ per day | 22.6 | (29.5, 120.1) |
| | | | |
| **Difference (Control – BioE4)** | 81.4 $mm^3$ per day | 32.6 | (16.0, 146.9) |
| | | | |

Figure 5

| | PBS (n=5) | | Bio96 (n=5) | | BioE4-03 (n=4) | |
|---|---|---|---|---|---|---|
| Day | Mean | Std Dev | Mean | Std Dev | Mean | Std Dev |
| 0 | 80.8 | 28.1 | 52.6 | 1.9 | 60.1 | 15 |
| 1 | 92.7 | 61.1 | 67.3 | 14.7 | 49.6 | 32.4 |
| 4 | 125.1 | 64.6 | 103.4 | 20.4 | 99.6 | 58.7 |
| 6 | 147.2 | 77.3 | 136.9 | 46.2 | 122.9 | 78 |
| 7 | 200.9 | 73.1 | 124.3 | 34.6 | 132.9 | 91.5 |
| 8 | 230.3 | 110.3 | 112.1 | 15.9 | 138.3 | 94.3 |
| 11 | 333.1 | 131.3 | 180.1 | 31.4 | 182.4 | 98.9 |
| 13 | 483.2 | 227.7 | 313.6 | 122.9 | 269 | 159.1 |
| 14 | 615.3 | 343.6 | 394.3 | 86.1 | 289.1 | 169.1 |
| 15 | 656.3 | 292.6 | 413.6 | 130.8 | 408.2 | 278.6 |
| 18 | 1104.2 | 617.2 | 548.2 | 215.5 | 547.3 | 310 |
| 20 | 900.8 | 96.4 | 693.9 | 262.4 | 620.9 | 362.7 |
| 21 | 1061.7 | 87.6 | 872.8 | 401.9 | 768.4 | 458.4 |

Figure 7

| Effect | Treatment | Estimate | Standard Error | DF | t Value | Pr > \|t\| |
|---|---|---|---|---|---|---|
| | | | | | | |
| Intercept | | 81.4676 | 139.95 | 11 | 0.58 | 0.5722 |
| Day | | -16.7560 | 14.3377 | 158 | -1.17 | 0.2443 |
| $Day^2$ | | 3.9965 | 0.6391 | 158 | 6.25 | <.0001 |
| Treatment | Bio96 | -27.5298 | 197.92 | 11 | -0.14 | 0.8919 |
| Treatment | BioE4-03 | -20.6341 | 209.93 | 11 | -0.10 | 0.9235 |
| Treatment | PBS | 0 | . | . | . | . |
| Day*Treatment | Bio96 | 4.0356 | 20.0487 | 158 | 0.20 | 0.8407 |
| Day*Treatment | BioE4-03 | 8.0387 | 21.2378 | 158 | 0.38 | 0.7056 |
| Day*Treatment | PBS | 0 | . | . | . | . |
| $Day^2$ x Treatment | Bio96 | -1.5371 | 0.8737 | 158 | -1.76 | 0.0804 |
| $Day^2$ x Treatment | BioE4-03 | -1.9786 | 0.9230 | 158 | -2.14 | 0.0336 |
| $Day^2$ x Treatment | PBS | 0 | . | . | . | . |

Figure 8

| | Model-Based Estimate of Mean Volume on Day 21 | Standard Error | 95% Confidence Interval for the Mean |
|---|---|---|---|
| | | | |
| **Control Group** | 1492.1 $mm^3$ | 145.3 | 1205.1, 1779.0 |
| **Bio96 Group** | 871.4 $mm^3$ | 140.0 | 595.0, 1147.8 |
| **BioE4-03 Group** | 767.7 $mm^3$ | 156.5 | 458.6, 1076.7 |
| | | | |
| **Difference (Control – Bio96)** | 620.7 $mm^3$ | 201.7 | 222.2, 1019.1 |
| **Difference (Control – BioE4-03)** | 724.4 $mm^3$ | 213.5 | 302.7, 1146.1 |
| | | | |
| | **Model-Based Estimate of Mean Rate of Increase in Volume on Day 21** | **Standard Error** | **95% Confidence Interval for the Mean** |
| | | | |
| **Control Group** | 151.1 $mm^3$ per day | 15.5 | 120.4, 181.8 |
| **Bio96 Group** | 90.6 $mm^3$ per day | 14.0 | 62.9, 118.3 |
| **BioE4-03 Group** | 76.0 $mm^3$ per day | 15.7 | 45.1, 107.0 |
| | | | |
| **Difference (Control – Bio96)** | 60.5 $mm^3$ per day | 20.9 | 19.2, 101.8 |
| **Difference (Control – BioE4-03)** | 75.1 $mm^3$ per day | 22.1 | 31.5, 118.6 |

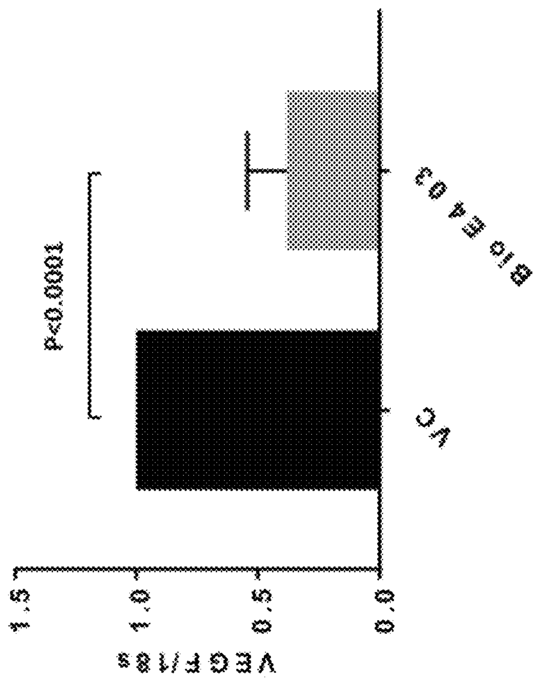
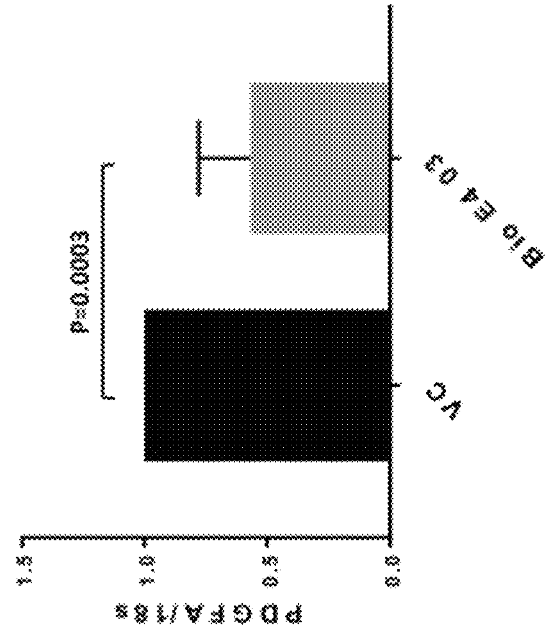
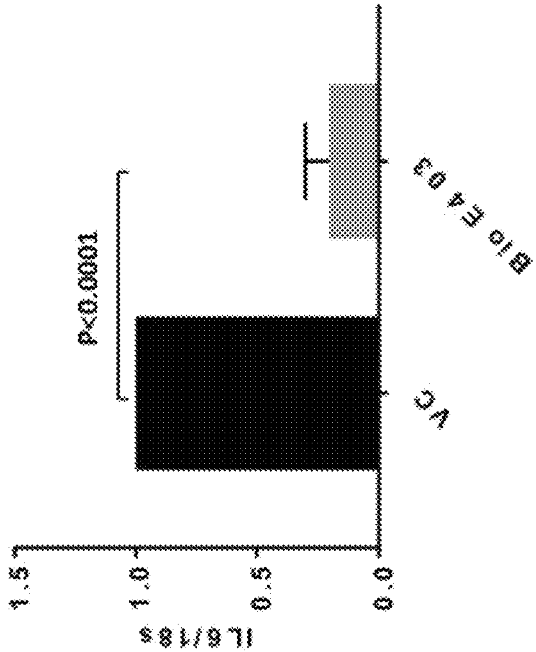
Figure 11 (cont.)

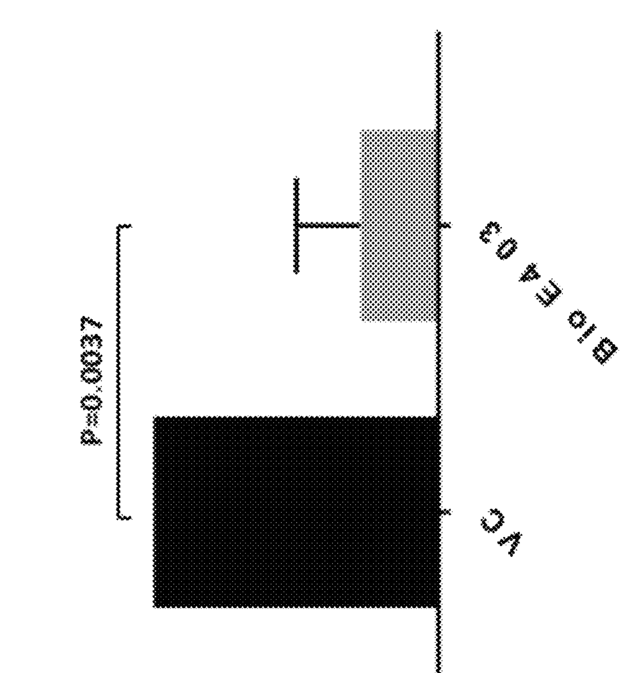
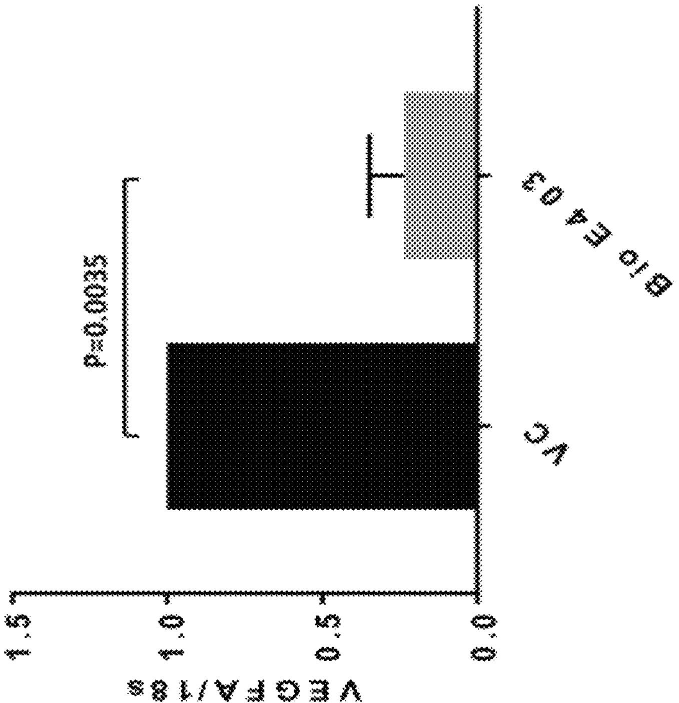
Figure 12 (cont.)

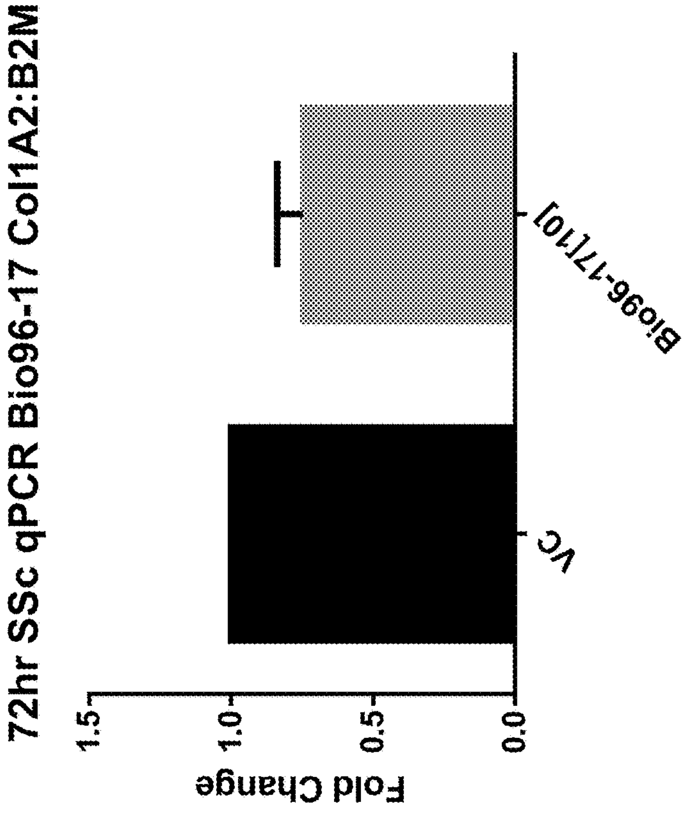
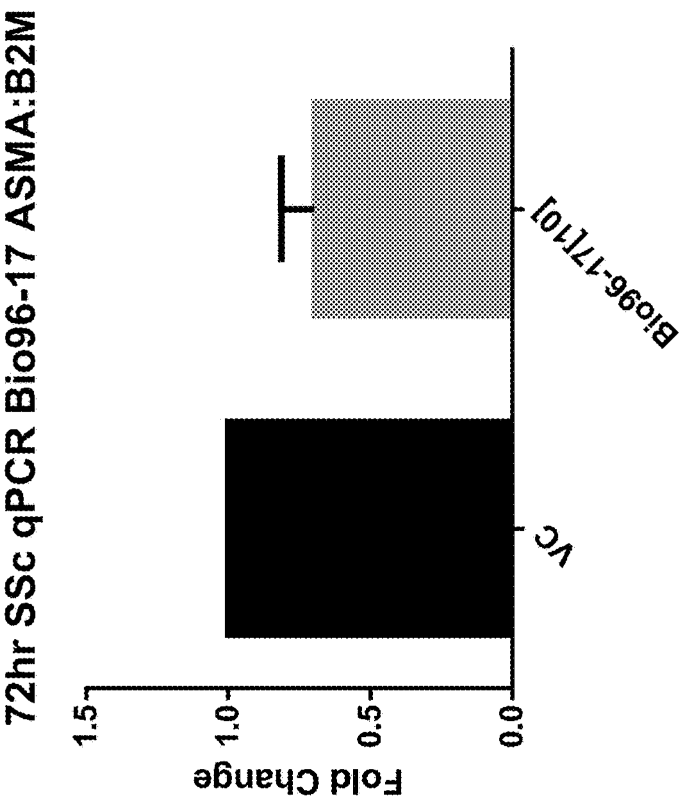
Figure 15

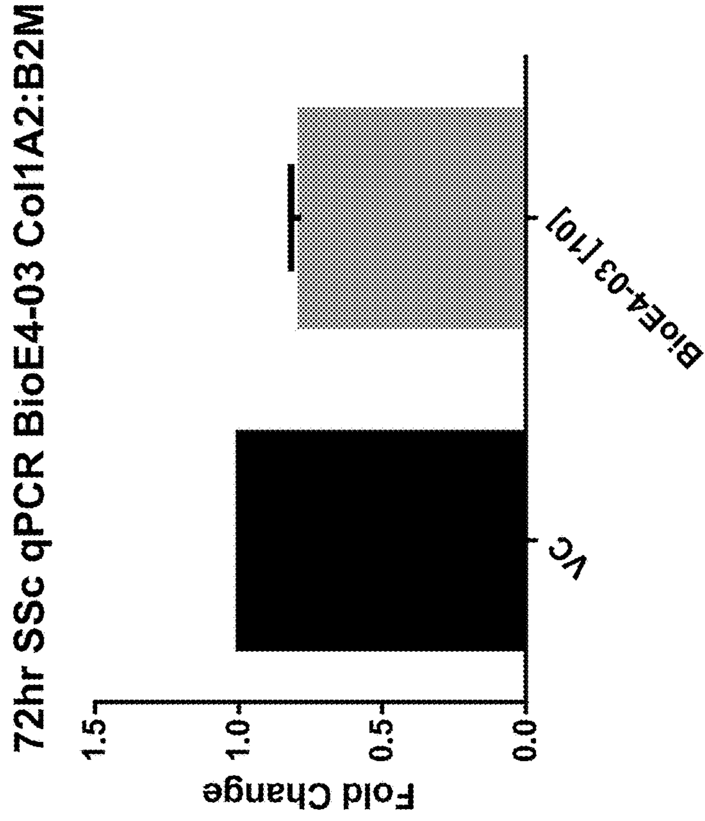
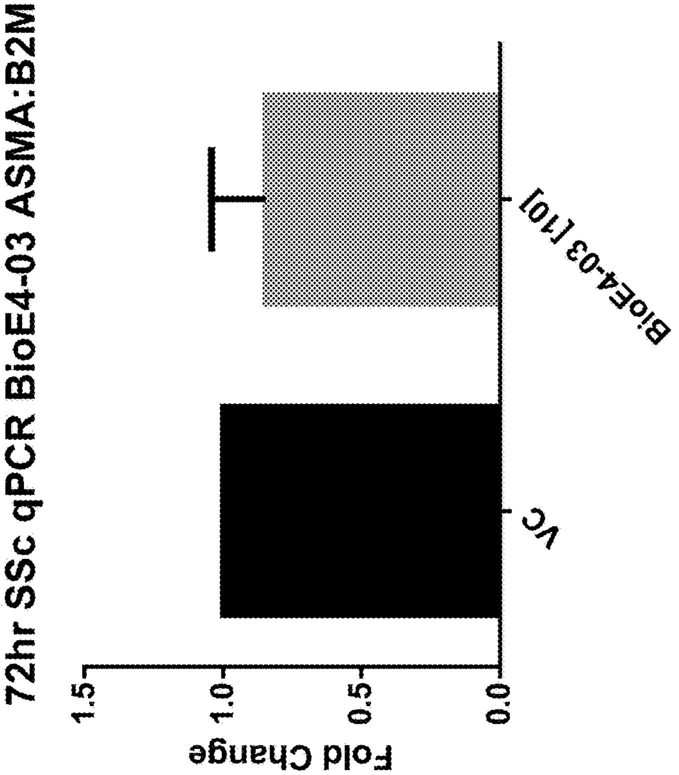
Figure 16

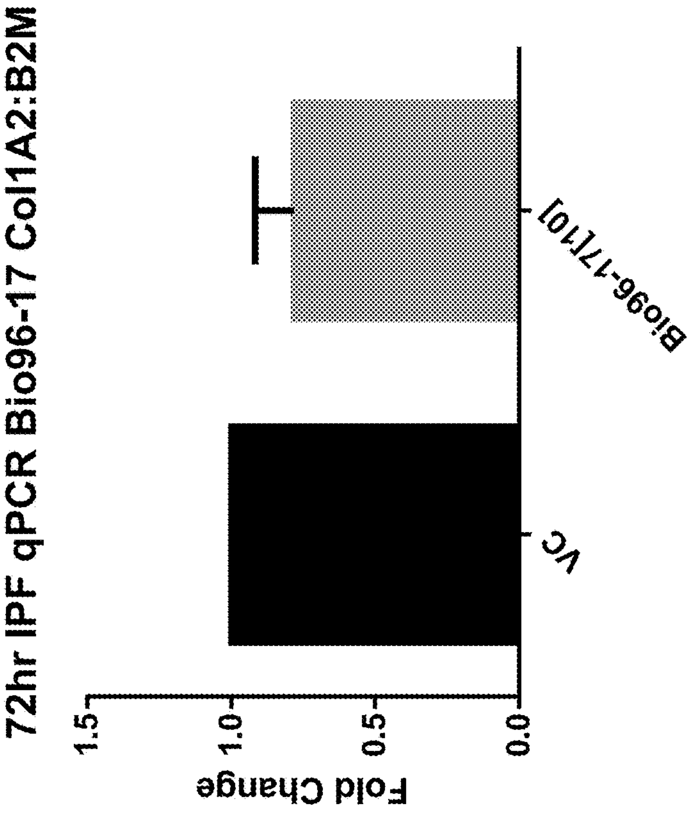
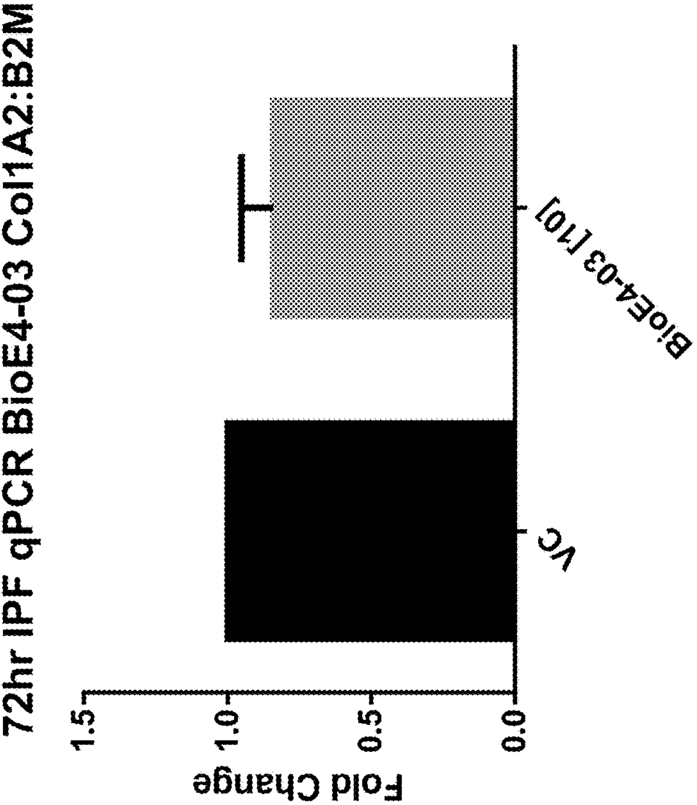
Figure 17

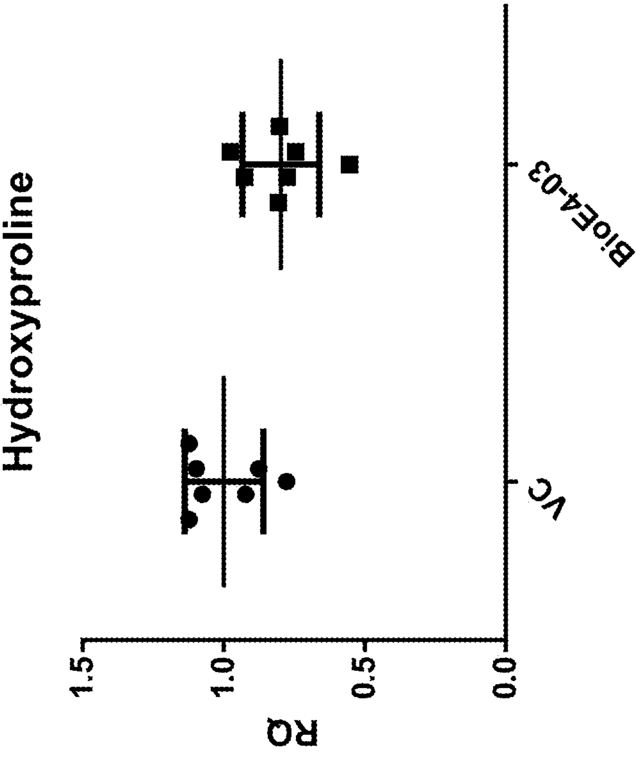
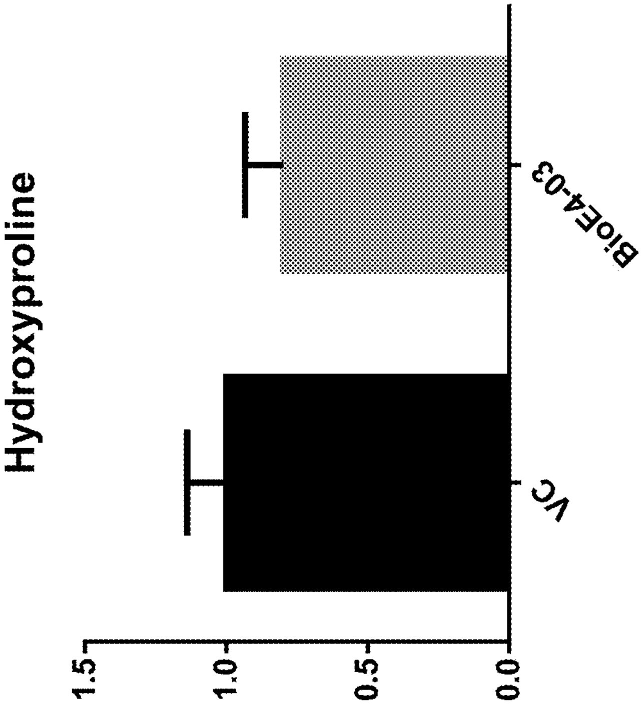
Figure 20

Figure 22

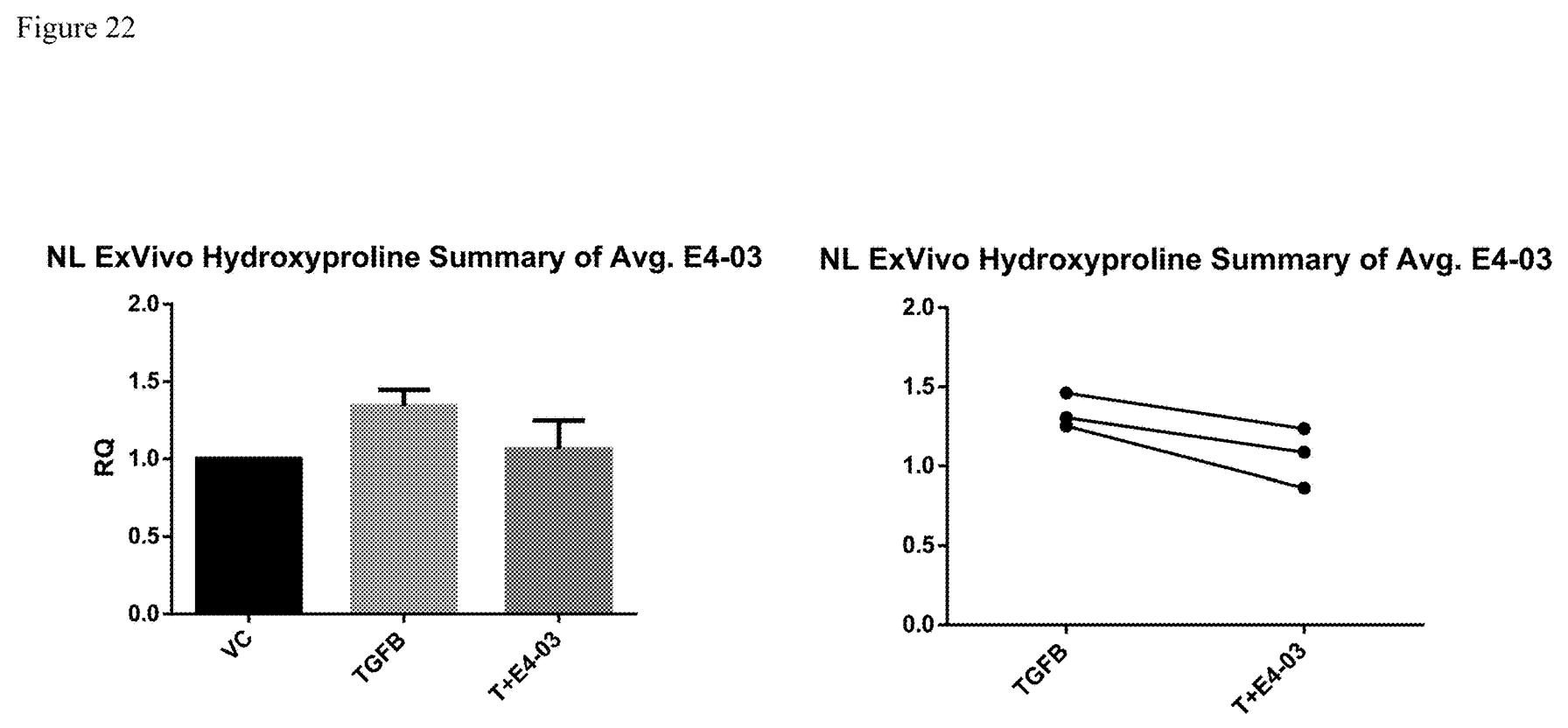

NL ExVivo Hydroxyproline Summary of Avg. E4-03

RQ 2.0
1.5
1.0
0.5
0.0

VC
TGFB
T+E4-03

NL ExVivo Hydroxyproline Summary of Avg. E4-03

2.0
1.5
1.0
0.5
0.0

TGFB
T+E4-03

Figure 23
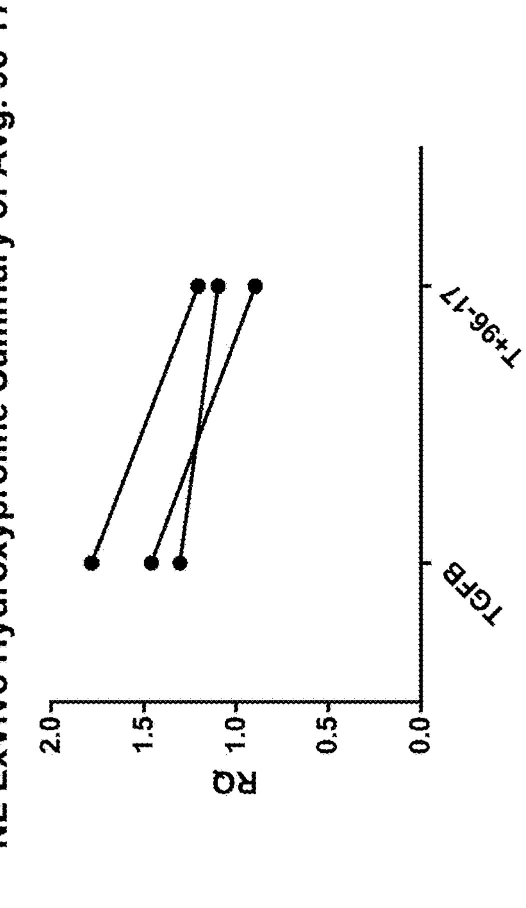
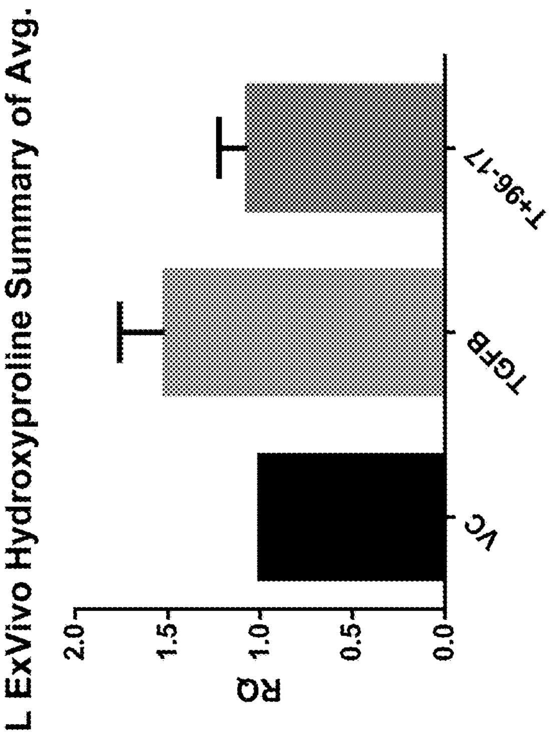

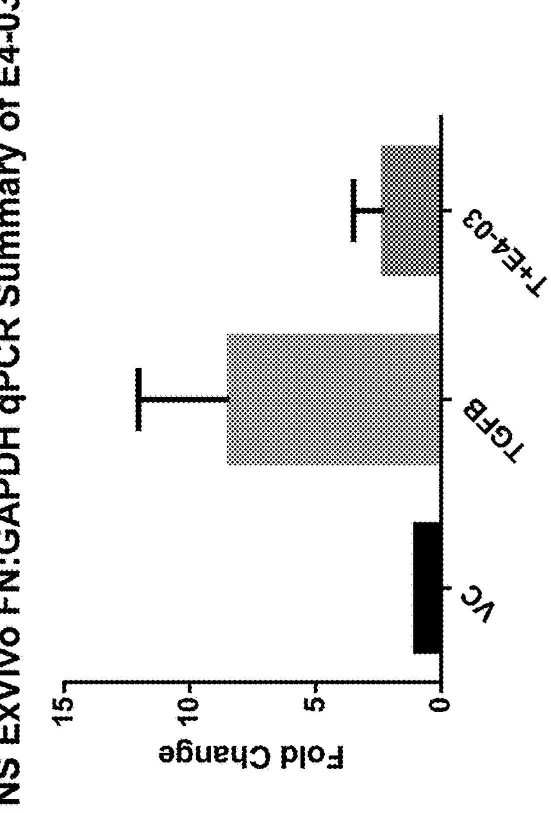
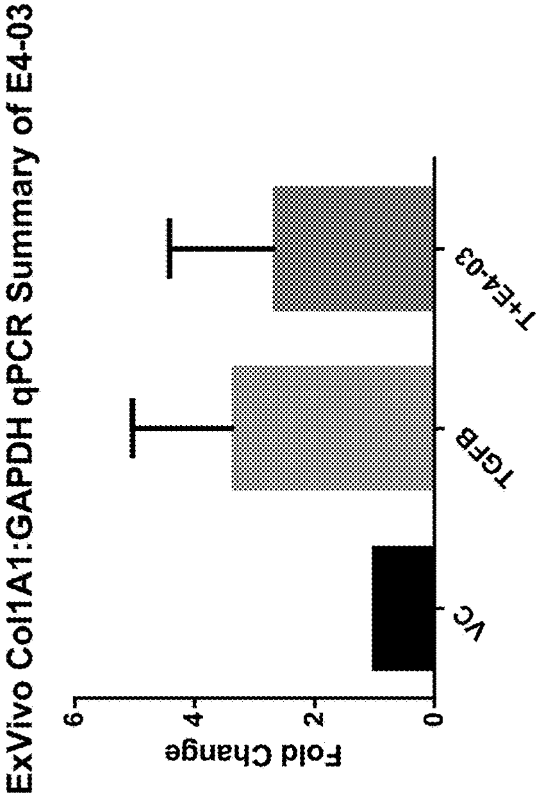
Figure 25

ENDOSTATIN PEPTIDES FOR THE TREATMENT OF TUMORS, FIBROSIS AND ACUTE LUNG INJURY

CROSS-REFERENCE TO RELATED APPLICATIONS

The present application claims priority to U.S. Provisional Patent Application No. 62/872,301, filed Jul. 10, 2019, which is hereby incorporated herein by reference in its entirety.

REFERENCE TO SEQUENCE LISTING

The present application hereby incorporates by reference the entire contents of the text file named "206085-0035-00_US_Sequence_Listing_ST25.txt" in ASCII format. The text file containing the Sequence Listing of the present application was created on Jul. 8, 2020 and is 2,885 bytes in size.

BACKGROUND OF THE INVENTION

The essence of many medical treatments and procedures involves the removal or destruction of harmful or unwanted tissue. Examples of such important treatments include the surgical removal of cancerous growths, the destruction of metastatic tumors through chemotherapy, and the reduction of glandular (e.g. prostate) hyperplasia.

There is an obvious need for an effective agent that will destroy and hence either facilitate the removal of or inhibit the further growth of harmful or unwanted cells and tissue but will have mainly local effects and minimal or absent systemic toxicity.

Endostatin, a 183 amino acid proteolytic cleavage fragment corresponding to the C-terminus of collagen 18, has anti-tumor activity with no toxic side effects (O'Reilly et al. (1997) Cell, 88: 277-285; Kisker et al. (2001) Cancer Res, 61:7669-7674; Dhanabal et al. (1999) Cancer Res, 59: 189-197; Yoon et al. (1999) Cancer Res, 59: 6251-6256; Folkman and Kalluri, (2003) Cancer Medicine, 6th edition, pp. 161-194. Hamilton: B. C. Decker Inc.). A number of anti-angiogenic activities have been reported for this protein, such as inhibition of endothelial cell proliferation, migration, and tube formation. This activity has been localized to the N-terminal region of endostatin. Endostatin also suppresses vascular endothelial growth factor (VEGF)-induced vascular permeability (Takahashi et al. (2003) Faseb J, 17: 896-898). Endostatin inhibits endothelial cell migration by inhibiting phosphorylation of focal adhesion kinase via binding to $\alpha 5\beta 1$ integrin (Wickstrom et al. (2002) Cancer Res, 62: 5580-5589). It also has been shown that cell surface glypicans are low-affinity endostatin receptors (Karumanchi et al. (2001) Mol Cell, 7: 811-822). Endostatin has been implicated in several signaling pathways, such as downregulation of c-myc (Shichiri and Hirata (2001) Faseb J, 15: 1044-1053), cyclin-D1 (Hanai et al. (2002) J Biol Chem, 277. 16464-16469) and RhoA activity (Wickstrom et al. (2003) J Biol Chem, 278: 37895-37901), blockage of VEGF signaling (Hajitou et al. (2002) Faseb J, 16: 1802-1804; Kim et al. (2002) J Biol Chem, 277: 27872-27879), and inhibition of the wnt-signaling pathway (Hanai et al. (2002) J Cell Biol, 158: 529-539). Furthermore, endostatin has been shown to bind and inactivate metalloproteinases (Kim et al. (2000) Cancer Res, 60: 5410-5413; Nyberg et al. (2003) J Biol Chem, 278: 22404-22411; Lee et al. (2002) FEBS Lett, 519: 147-152) and to regulate a spectrum of genes which suppress angiogenesis (Abdollahi et al. (2004) Mol Cell, 13: 649-663).

The crystal structures of both murine and human endostatin have been resolved (Hohenester et al. (1998) Embo J, 17: 1656-1664; Ding et al. (1998) Proc Natl Acad Sci USA, 95: 10443-10448) and show a noncovalently held dimer at high concentration required for crystallization (Ding et al. (1998) Proc Natl Acad Sci USA, 95: 10443-10448). The presence of two disulfide bonds results in a highly folded structure. Endostatin binds one atom of zinc per monomer via the three histidines in the N-terminus of the molecule (histidines 1, 3, and 11) and aspartatic 76. The heparin binding property of endostatin is mediated by noncontiguous arginines clustered over the three dimensional globular surface of the molecule (Sasaki et al. (1999) Embo J, 18: 6240-6248).

Oligomeric endostatin (NC1 and dimer) have been shown to be primarily associated with laminin in the basement membrane (Javaherian et al. (2002) J Biol Chem, 277: 45211-45218). This association may be important for some of the biological functions displayed by endostatin. On the other hand, the heparin binding properties of endostatin manifest themselves in its interaction with the cell surface. It is likely that endostatin has a number of biological functions mediated by different regions of the protein.

Thus, there is a need in the art for new and less toxic compositions and methods for treating tumor growth, fibrosis, and acute lung injury. The present invention satisfies this unmet need.

SUMMARY OF THE INVENTION

In one embodiment, the invention provides a composition comprising a therapeutic agent having an anti-tumor activity, an anti-fibrotic activity, anti-lung injury activity or a combination thereof, wherein the agent is a C-terminal endostatin-derived peptide, an isolated nucleic acid encoding a C-terminal endostatin-derived peptide, or variants, derivatives, mutants, or fragments thereof.

In one embodiment, the C-terminal endostatin-derived peptide comprises an amino acid sequence selected from the group consisting of at least one of SEQ ID NOs: 1-7, fragments thereof and variants thereof.

In one embodiment, the C-terminal endostatin-derived peptide variant comprises at most 5 amino acid substitutions.

In one embodiment, the C-terminal endostatin-derived peptide variant comprises a consecutive amino acid.

In one embodiment, the C-terminal endostatin-derived peptide fragment comprises at least 8 consecutive amino acids of an amino acid sequence of SEQ ID NO:1-7.

In one embodiment, the therapeutic further comprises a second agent, wherein the second agent is an anti-cancer agent.

In one embodiment, the therapeutic further comprises a second agent, wherein the second agent is an anti-fibrotic agent.

The invention also provides a method of treating or preventing a disease or disorder in a subject in need thereof. In one embodiment, the method comprises administering to the subject an effective amount of a composition comprising an agent, wherein the agent is selected from the group consisting of a C-terminal endostatin-derived peptide, an isolated nucleic acid encoding a C-terminal endostatin-derived peptide, and variants, derivatives, mutants, fragments thereof.

In one embodiment, the disease or disorder is cancer. In one embodiment, the cancer is prostate cancer, lung cancer, breast cancer, liver cancer, ovarian cancer, endometrial cancer, bladder cancer, colon cancer, lymphoma, skin cancer, pancreatic cancer, gastric cancer, myeloma or glioma. In one embodiment, the method further comprises administering a second agent, wherein the second agent is an anticancer agent.

In one embodiment, the disease or disorder is a fibrotic or fibrotic-related disease or disorder. In one embodiment, the fibrotic or fibrotic-related disease or disorder is cardiac fibrosis, idiopathic pulmonary fibrosis, interstitial pulmonary fibrosis, familial pulmonary fibrosis, radiation-induced pulmonary fibrosis, Coal workers' pneumoconiosis, asbestosis, bleomycin lung, sarcoidosis, silicosis, acute lung injury, ARDS, hypertrophic scars, keloid scars, liver cirrhosis, systemic scleroderma, localized scleroderma, morphea, vascular fibrosis, kidney fibrosis, fibrosis as a result of Graft-Versus-Host Disease (GVHD), subepithelial fibrosis, endomyocardial fibrosis, uterine fibrosis, myelofibrosis, retroperitoneal fibrosis, nephrogenic systemic fibrosis, scarring after surgery, asthma, glomerulonephritis, multifocal fibrosclerosis, diabetic nephropathy, rheumatoid arthritis, atherosclerosis, radiation-induced fibrosis, chemo-therapy induced fibrosis, systemic sclerosis, hepatitis and Sjogren syndrome. In one embodiment, the method further comprises administering a second agent, wherein the second agent is an anti-fibrotic agent.

In one embodiment, the disease or disorder is acute lung injury. In one embodiment the acute lung injury is acute respiratory distress syndrome (ARDS), virus-induced acute lung injury, SARS, COVID-19, influenza-induced acute lung injury, acute lung injury due to sepsis, acute lung injury due to pneumonia, acute lung injury due to aspiration, acute lung injury due to trauma, acute lung injury due to blood transfusion, acute lung injury due to smoke, acute lung injury due to toxic gas inhalation, acute lung injury due to pancreatitis, acute lung injury due to drug overdose, acute lung injury due to burn, and ventilator-associated lung injury, manifesting with inflammation.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the results of example experiments demonstrating descriptive statistics for the raw tumor volumes over time in the control (n=4) and BioE4 groups (n=5, days 0-5; n=4, days 7-15) of mice. Volume measurements are in mm.

FIG. 3 depicts the results of example experiments demonstrating parameter estimates for the general linear mixed model. BioE4 is an indicator variable, where 1 represents the BioE4 group and 0 represents the Control group.

FIG. 4 depicts the results of example experiment, using the model described above, whereas direct comparisons were made between BioE4 and Control with respect to the mean tumor volumes at day 15 and the mean rate of change in the tumor volumes at day 15. Model-based estimates at day 15 shows that the mean tumor volume was significantly (p=0.0001) greater in the Control group when compared to the BioE4 group, and the mean rate of increase in the volume on day 15 was also significantly (p=0.02) greater in the Control group when compared to the BioE4 group.

FIG. 5 depicts the results of example experiments and descriptive statistics for the raw tumor volumes over time in the PBS (n=5), Bio96 (n=5), and BioE4-03 groups (n=4) of mice. Volume measurements are in mm.

FIG. 7 depicts the results of example experiments demonstrating parameter estimates for the general linear mixed model parameter estimates for the general linear mixed model comparing PBS to Bio96 and Bio96E4-03.

FIG. 8 depicts the results of example experiment, using the model described above, whereas direct comparisons were made between the PBS Control and Bio96 and between PBS and BioE4-03 with respect to the mean tumor volumes at day 21 and the mean rate of change in the tumor volumes at day 21. Model-based estimates at day 21 shows that the mean tumor volume was significantly greater in the PBS control group when compared to the Bio96 group (1492.1 $mm^3$ vs. 871.4 $mm^3$, p=0.003), and the mean tumor volume was significantly greater in the PBS control group when compared to the BioE4-03 group (1492.1 $mm^3$ vs. 767.7 $mm^3$, p=0.0009). At day 21, the mean rate of increase in the volume was significantly greater in the PBS control group when compared to the Bio96 group (151.1 $mm^3$ per day vs. 90.6 $mm^3$ per day, p=0.004), and the mean rate of increase in the volume was significantly greater in the PBS control group when compared to the BioE4-03 group (151.1 $mm^3$ per day vs. 76.0 $mm^3$ per day, p=0.0008).

FIG. 15 depicts an exemplary analysis of gene expression in fibroblasts from lungs of patients with systemic sclerosis (SSc) treated with Bio96-17.

FIG. 16 depicts an exemplary analysis of gene expression in fibroblasts from lungs of patients with SSc treated with BioE4-03.

FIG. 17 depicts an exemplary analysis of gene expression in fibroblasts from lungs of patients with idiopathic pulmonary fibrosis (IPF) treated with BioE4-03 or Bio96-17.

FIG. 20 depicts an exemplary analysis of hydroxyproline levels in lung tissues of patients with SSc in organ culture treated with BioE4-03.

FIG. 22 depicts an exemplary analysis of hydroxyproline levels in lung tissues of normal donors in organ culture treated with BioE4-03.

FIG. 23 depicts an exemplary analysis of hydroxyproline levels in lung tissues of normal donors in organ culture treated with Bio96-17.

FIG. 25 depicts an exemplary analysis of Col1A1 and fibronectin (FN) gene expression in skin tissues from donors in which fibrosis was induced with TGFbeta, treated with BioE4-03.

FIG. 28A depicts the effect Biotinylated E4-03 on IL-6 mRNA in human lung adenocarcinoma cells (A549). FIG. 28B depicts the effect of Non-biotinylated E4-03 on IL-6 mRNA and protein expression in A549 cells. A549 cells were treated with BioE4-03 or E4-03 for 48 hours prior to qPCR analysis for mRNA expression and 72 hours prior to ELISA analysis for protein expression.

DETAILED DESCRIPTION

Figure 2B:
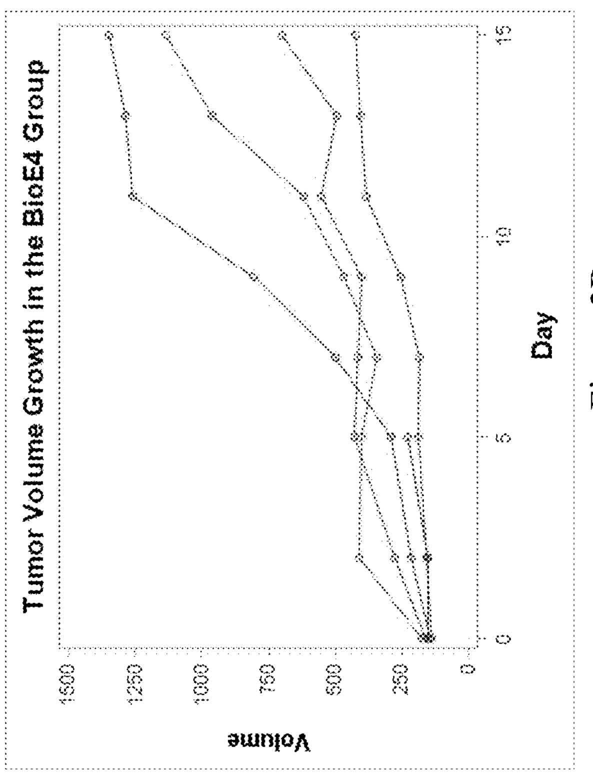
FIG. 2A and FIG. 2B depict the results of example experiments demonstrating mouse-specific tumor growth trajectories, separated for the Control and BioE4 groups.

In one aspect, the present invention is directed to methods and compositions for treatment, inhibition, prevention or reduction of tumor growth. In another aspect, the present invention is directed to methods and compositions for treatment, inhibition, prevention or reduction of fibrosis or fibrotic-related diseases or disorders. In one aspect, the present invention is directed to methods and compositions for treatment, inhibition, prevention or reduction of a combination of tumor growth and fibrosis or fibrotic-related diseases or disorders. In another aspect, the present invention is directed to methods and compositions for treatment, inhibition, prevention or reduction of acute lung injury. In one embodiment, the composition comprises an agent, for example, an isolated nucleic acid, isolated peptide, small molecule, peptidomimetic, or the like, that are derived from the C-terminal region of endostatin. In one embodiment, the composition comprises fragments derived from the C-terminal region of full-length endostatin. In one embodiment, the composition comprises recombinant fragments derived from the C-terminal region of endostatin.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A disease or disorder is "alleviated" if the severity of a sign or symptom of the disease or disorder, the frequency with which such a sign or symptom is experienced by a patient, or both, is reduced. "Alleviating" specific cancers and/or their pathology includes degrading a tumor, for example, breaking down the structural integrity or connective tissue of a tumor, such that the tumor size is reduced when compared to the tumor size before treatment. "Alleviating" metastasis of cancer includes reducing the rate at which the cancer spreads to other organs.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, gastric cancer, myeloma, colorectal cancer, renal cancer, liver cancer, brain cancer, lymphoma, leukemia, lung cancer, sarcoma and the like.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein the terms "fibrotic disease", "fibrotic disorder", "fibrotic-related disease" and "fibrotic-related disorder" refer to conditions involving fibrosis in one or more tissues. As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. As used herein the term "fibrosis" is used synonymously with "fibroblast accumulation and collagen deposition".

The term "anti-fibrotic" activity as used herein refers to the ability of an active substance to prevent an excessive pathologic accumulation of collagenous scar or connective tissue in various body structures and organs (usually triggered by some injury, allergy, infection, or by some inherited genetic aberration), or to promote the non-surgical removal or biological dissolution of an existing excessive and pathologic accumulation of fibrotic collagenous tissue.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "inhibit," as used herein, means to suppress or block an activity or function by at least about ten percent relative to a control value. In some instances, the activity is suppressed or blocked by 50%, 75%, 90%, or 95% compared to a control value.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient.

The phrase "therapeutically effective amount," as used herein, refers to an amount that is sufficient or effective to prevent or treat (delay or prevent the onset of, prevent the progression of, inhibit, decrease or reverse) a disease, disorder or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based in part on the discovery that peptides derived from the C-terminal region of endostatin can be used for the treatment or prevention of tumor growth, fibrosis, and acute lung injury. Accordingly, in one embodiment, the invention includes compositions comprising C-terminal endostatin peptides, polypeptides, fragments and the likes having anti-tumor activity, anti-fibrotic activity, anti-lung injury activity or a combination thereof. In one embodiment, nucleotides encoding these peptides, host cells transformed with the nucleotides, and methods of using these peptides and nucleotides are included in the invention.

In one embodiment, the invention provides compositions for inhibiting tumor growth, fibrosis, acute lung injury, or a combination thereof. For example, the present invention is based in part upon the identification of the region within endostatin which inhibits tumor growth, fibrosis, and acute lung injury. It is demonstrated herein that endostatin fragments and endostatin-derived peptides thereof mimic endostatin in inhibiting tumor growth and fibrosis. Further, it is demonstrated herein that endostatin fragments and endostatin-derived peptides thereof reduce the level of IL-6, which is increased in lung tissue of subject with acute lung injury and promotes cytokine storm.

In certain embodiments, the endostatin-derived peptide comprises an amino acid sequence of:

96: (SEQ ID NO: 1)
ATGQASSLL,

E4-03: (SEQ ID NO: 2)
SYCETWRTEAPSATGQASSLLGGRLLGQSAASCHHA,

E4: (SEQ ID NO: 3)
SYCETWRTEAPSATGQASSLLGGRLLGQSAASCHHAYIVLCIENSFMT, 96-17: (SEQ ID NO: 4)
ATGQASSLLGGRLLGQSAASCHHA, 96-87: (SEQ ID NO: 5)
ATGQASSLLGGRLLGQ, 91-96: (SEQ ID NO: 6)
SYCETWRTEAPSATGQASSLL, 91-97, (SEQ ID NO:7)
SYCETWRTEAPSATGQASSLLGGRLLGQ, or a variant or fragment thereof.

In one embodiment, the invention provides a method for treating or preventing tumor growth. The method can be used for treating or preventing, for example, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

In one embodiment, the invention provides a method for treating or preventing fibrosis. The method can be used for treating or preventing, for example, fibrosis of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

In one embodiment, the invention provides a method for treating or preventing acute lung injury. It is demonstrated herein that endostatin fragments and endostatin-derived peptides thereof reduce IL-6 secretion from lung-derived cells. IL-6 levels are increased in lung tissues of patients with acute lung injury and promote cytokine storm. Thus, the present invention provides a method for treating acute lung injury, ARDS, virus-induced acute lung injury, SARS, COVID-19, influenza-induced acute lung injury, acute lung injury due to sepsis, pneumonia, aspiration, trauma, blood transfusions, smoke, toxic gas inhalation, pancreatitis, drug overdoses, burns, and other lung injury or acute respiratory distress syndromes, including ventilator-associated lung injury, manifesting with inflammation.

Compositions

In one aspect, the present invention provides compositions comprising an agent derived from the C-terminal region of endostatin having anti-tumor activity, anti-fibrotic activity, or a combination thereof. Exemplary agents, include, but are not limited to, isolated nucleic acids, vectors, isolated peptides, peptide mimetics, small molecules, and the like.

In one embodiment, the composition of the present invention comprises an isolated peptide derived from the C-terminal region of endostatin, or biologically functional fragment thereof. The composition may comprise, for example, any isoform of a C-terminal endostatin peptide of the invention, including endostatin from any organism.

In certain embodiments, the isolated peptide of the composition comprises an amino acid sequence of:

96: (SEQ ID NO: 1)
ATGQASSLL,

E4-03: (SEQ ID NO: 2)
SYCETWRTEAPSATGQASSLLGGRLLGQSAASCHHA,

E4: (SEQ ID NO: 3)
SYCETWRTEAPSATGQASSLLGGRLLGQSAASCHHAYIVLCIENSFMT 96-17: (SEQ ID NO: 4)
ATGQASSLLGGRLLGQSAASCHHA, 96-87: (SEQ ID NO: 5)
ATGQASSLLGGRLLGQ, 91-96: (SEQ ID NO: 6)
SYCETWRTEAPSATGQASSLL, 91-97, (SEQ ID NO: 7)
SYCETWRTEAPSATGQASSLLGGRLLGQ, or a variant or fragment thereof.

In one embodiment, the peptide is biotinylated at the N-terminus, amidated at the C-terminus, or a combination thereof.

In certain instances, as described herein, N-terminally biotinylated peptides are presented with a "Bio" prefix. Thus, in one embodiment, Bio96 refers to SEQ ID NO:1 being biotinylated at its N-terminus. In one embodiment, BioE4-03 refers to SEQ ID NO:2 being biotinylated at its N-terminus. In one embodiment, BioE4 refers to SEQ ID NO:3 being biotinylated at its N-terminus. In one embodiment, Bio96-17 refers to SEQ ID NO:4 being biotinylated at its N-terminus. In one embodiment, Bio96-87 refers to SEQ ID NO:5 being biotinylated at its N-terminus. In one embodiment, Bio91-96 refers to SEQ ID NO:6 being biotinylated at its N-terminus. In one embodiment, Bio91-97 refers to SEQ ID NO:7 being biotinylated at its N-terminus. In certain embodiments, a biotinylated peptide, as described herein, is amidated at the C-terminus.

In one embodiment, the composition comprises fragments of full-length endostatin derived from the m region of endostatin. Fragments of full-length C-terminal region endostatin peptides include, but are not limited to, fragments of SEQ ID NO:1-7 comprising at least 5, 6, 7, 8, 9, 10 11, 12, 13, 14, 15, 16, 17, 18, 19, 20, 21, 22, 23, 24, 25, 26, 27, 28, 29, 30, 31, 32, 33, 34, or 35 consecutive amino acids of a full-length C-terminal region endostatin peptide as set forth in SEQ ID NO:1-7. In one embodiment, the composition comprises a recombinant C-terminal fragment of endostatin.

In one embodiment, the invention includes C-terminal endostatin polypeptides and variants thereof. In one embodiment, the endostatin-derived peptide comprises a fragment of endostatin that mimics the ability of endostatin to inhibit tumor growth, fibrosis, or a combination thereof. In one embodiment, the endostatin-derived peptide comprises a fragment of endostatin that reduces, treats, or prevents acute lung injury. In one embodiment, the endostatin-derived peptide comprises a derivative of the endostatin fragment.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

In one embodiment, the invention includes any form of a peptide comprising amino acids derived from the C-terminal region of an endostatin protein, but does not include full length endostatin protein, or the N-terminal region of an endostatin protein. In one embodiment, the invention includes amino acid sequences having substantial homology to C-terminal endostatin or a C-terminal endostatin-derived peptide disclosed herein. In certain embodiments, a peptide which is "substantially homologous" is about 50% homologous, about 70% homologous, about 80% homologous, about 85% homologous, about 90% homologous, about 91% homologous, about 92% homologous, about 93% homologous, about 94% homologous, about 95% homologous, about 96% homologous, about 97% homologous, about 98% homologous, or about 99% homologous to amino acid sequence of the C-terminal region of endostatin.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag or immunoglobulin Fc region). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to inhibit tumor growth, fibrosis, or a combination thereof. The present invention includes amino acid sequences that are at least 60%, 65%, 70%, 72%, 74%, 76%, 78%, 80%, 82%, 84%, 86%, 88%, 90%, 91%, 92%, 93%, 94%, 95%, 96%, 97%, 98%, or 99% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, phosphorylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the anti-tumor activity, anti-fibrotic activity, or combination thereof, of the C-terminal endostatin peptides of the invention. In one embodiment, the peptide or protein of the invention may be fused to biotin.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising amino acids of the C-terminal region of an endostatin protein, but does not include a full length endostatin protein, or the N-terminal region of an endostatin protein whereby the peptide can be fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., tumor antigen). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the C-terminal endostatin peptide or endostatin-derived peptide fused to the selected protein or marker protein as described herein. Examples of proteins which may be used to prepare fusion proteins include immunoglobulins, glutathione-S-transferase (GST), hemagglutinin (HA), and truncated myc. For example, a polypeptide, may be linked to a CH1, CH2 and/or CH3 domain of a heavy chain. If the constant region is from a light chain, it can be from a kappa or lambda light chain. If the constant region is from a heavy chain, it can be from an antibody of any one of the following classes of antibodies: IgG, IgA, IgE, IgD, and IgM. IgG can be an $IgG_1$, $IgG_2$, $IgG_3$ or $IgG_4$. The constant domain may be an Fc fragment. The constant domain can be from a mammalian antibody, such as a human antibody. Soluble receptor-IgG fusion proteins are common immunological reagents and methods for their construction are known in the art (see, for example, U.S. Pat. Nos. 5,225,538, 5,726,044; 5,707,632; 750,375, 5,925,351, 6,406,697 and Bergers et al. Science 1999 284: 808-12). In one example, the immunoglobulin is the constant part of the heavy chain of human IgG, particularly $IgG_1$, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

In one embodiment, the present invention provides a composition comprising an isolated nucleic acid encoding C-terminal endostatin, an endostatin-derived peptide, or a biologically functional fragment thereof.

In one embodiment, the isolated nucleic acid sequence encodes C-terminal endostatin. In various embodiments, the isolated nucleic acid sequence encodes an endostatin-derived peptide comprising an amino acid sequence of:

```
96:
                                          (SEQ ID NO: 1)
ATGQASSLL,

E4-03:
                                          (SEQ ID NO: 2)
SYCETWRTEAPSATGQASSLLGGRLLGQSAASCHHA,
```

-continued

E4:

(SEQ ID NO: 3)
SYCETWRTEAPSATGQASSLLGGRLLGQSAASCHHAYIVLCIENSFMT, 96-17:

(SEQ ID NO: 4)
ATGQASSLLGGRLLGQSAASCHHA, 96-87:

(SEQ ID NO: 5)
ATGQASSLLGGRLLGQ, 91-96:

(SEQ ID NO: 6)
SYCETWRTEAPSATGQASSLL, 91-97, (SEQ ID NO: 7)
SYCETWRTEAPSATGQASSLLGGRLLGQ, or a variant or fragment thereof. In one embodiment, the peptide is biotinylated at the N-terminus, amidated at the C-terminus, or a combination thereof.

Further, the invention encompasses an isolated nucleic acid encoding a peptide having substantial homology to C-terminal endostatin or a endostatin-derived peptide disclosed herein. In certain embodiments, the isolated nucleic acid sequence encodes C-terminal endostatin or an endostatin-derived peptide having at least 75%, 80%, 85%, 90%, 91%, 92%, 93%, 94%, 95%, 96%, 97%, 98%, or 99% sequence homology with an amino acid sequence selected from SEQ NOs: 1-7.

The isolated nucleic acid sequence encoding C-terminal endostatin or an endostatin-derived peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding C-terminal endostatin or an endostatin-derived peptide, or functional fragment thereof. In one embodiment, the composition comprises an isolated RNA molecule encoding C-terminal endostatin or an endostatin-derived peptide, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the invention preferably has one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding C-terminal endostatin or an endostatin-derived peptide is typically achieved by operably linking a nucleic acid encoding the C-terminal endostatin or an endostatin-derived peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In one embodiment, a replication-deficient adenovirus can be used. In one embodiment, replication-deficient serotype 5 adenovirus can be used.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor—1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of C-terminal endostatin or an endostatin-derived peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR, RT-qPCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising C-terminal endostatin or an endostatin-derived peptide, or a nucleic acid molecule encoding C-terminal endostatin or an endostatin-derived peptide. Exemplary delivery vehicles include, but are not limited to, microspheres, microparticles, nanoparticles, polymerosomes, liposomes, and micelles. For example, in certain embodiments, the delivery vehicle is loaded with C-terminal endostatin or an endostatin-derived peptide, or a nucleic acid molecule encoding C-terminal endostatin or an endostatin-derived peptide. In certain embodiments, the delivery vehicle provides for controlled release, delayed release, or continual release of its loaded cargo. In certain embodiments, the delivery vehicle comprises a targeting moiety that targets the delivery vehicle to a treatment site.

The present invention also provides a scaffold or substrate composition comprising C-terminal endostatin or an endostatin-derived peptide, a nucleic acid molecule encoding C-terminal endostatin or an endostatin-derived peptide, a cell producing C-terminal endostatin or an endostatin-derived peptide, or a combination thereof. In another embodiment, C-terminal endostatin or an endostatin-derived peptide, a cell producing C-terminal endostatin or an endostatin-derived peptide, a nucleic acid molecule encoding C-terminal endostatin or an endostatin-derived peptide, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, intratracheal or intraperitoneal injection, inhalation, infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, fish oils and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Methods of Treatment of Tumors

In one embodiment, the C-terminal endostatin or an endostatin-derived peptide of the invention reduces production of extracellular matrix proteins by fibroblasts in fibrotic lungs and skin. Cancer associated fibroblasts (CAF) also cause fibrosis. Therefore, in various embodiments, the C-terminal endostatin or an endostatin-derived peptide of the invention can be used for treatment or prevention of cancer, fibrotic diseases, or a combination thereof.

In one embodiment, the present invention provides a method for the treatment or prevention tumor growth in a subject in need thereof. Exemplary conditions treated or prevented by way of the present invention include, but are not limited to, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

In one embodiment, the invention provides methods for preventing metastasis of malignant tumors or other cancerous cells as well as to reduce the rate of tumor growth. The methods comprise administering an effective amount of one or more of the disclosed compounds to a subject diagnosed with a malignant tumor or cancerous cells or to a subject having a tumor or cancerous cells. In one embodiment, the method comprises administering to a subject a composition comprising a C-terminal endostatin or an endostatin-derived peptide, or nucleic acid molecule encoding a C-terminal endostatin or endostatin-derived peptide, as described herein.

In one embodiment, the endostatin peptides of the invention are used for the treatment or prevention of a lung cancer or a skin cancer. However the invention is not limited to the treatment of lung cancer. The following are non-limiting examples of cancers that can be treated or prevented by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilm's tumor.

Methods for Treatment of Fibrosis

One aspect of the invention provides a method of treating or preventing fibrosis, a fibrotic-related disease or disorder or a cardiovascular disease or disorder, comprising administering to a subject a composition comprising a C-terminal endostatin or an endostatin-derived peptide, or nucleic acid molecule encoding a C-terminal endostatin or endostatin-derived peptide, as described herein. In one embodiment, fibrotic-related disease or disorders include, but are not limited to, cardiac fibrosis, interstitial lung diseases, idiopathic pulmonary fibrosis, interstitial pulmonary fibrosis, familial pulmonary fibrosis, radiation-induced pulmonary fibrosis, Coal workers' pneumoconiosis, asbestosis, bleomycin lung, sarcoidosis, silicosis, acute lung injury, ARDS, wound healing diseases or disorders, hypertrophic scars, keloid scars, liver cirrhosis, systemic scleroderma, localized scleroderma, including but not limited to morphea, vascular fibrosis, kidney fibrosis, fibrosis as a result of Graft-Versus-Host Disease (GVHD), subepithelial fibrosis, endomyocardial fibrosis, uterine fibrosis, myelofibrosis, retroperitoneal fibrosis, nephrogenic systemic fibrosis, scarring after surgery, asthma, glomerulonephritis, multifocal fibrosclerosis, diabetic nephropathy, rheumatoid arthritis, atherosclerosis, radiation-induced fibrosis, chemo-therapy induced fibrosis, systemic sclerosis, hepatitis and Sjogren syndrome.

In one embodiment, fibrotic-related disease or disorders include, but are not limited to, cardiac fibrosis. In one embodiment, cardiac fibrosis results from a cardiac injury. For example, in one embodiment cardiac fibrosis results from an injury including, but not limited to, myocardial infarction, aortic stenosis, restrictive cardiomyopathy, systemic and pulmonary hypertension, or carcinoid heart disease. In one embodiment, interstitial lung diseases include, but are not limited to idiopathic pulmonary fibrosis, interstitial pulmonary fibrosis, Coal workers' pneumoconiosis, asbestosis, acute lung injury and ARDS. In one embodiment, wound healing diseases and disorders include, but are not limited to, hypertrophic scars, keloid scars.

In one embodiment, fibrosis includes the formation or development of excess fibrous connective tissue in an organ or tissue as a reparative or reactive process, as opposed to a formation of fibrous tissue as a normal constituent of an organ or tissue. Skin and lungs are susceptible to fibrosis.

In some instances, fibrotic diseases are characterized by the activation of fibroblasts, increased production of collagen and fibronectin, and transdifferentiation into contractile myofibroblasts. This process usually occurs over many months and years, and can lead to organ dysfunction or death. Fibrotic-related diseases and disorders represents one of the largest groups of disorders for which there is no effective therapy and thus represents a major unmet medical need. Often the only redress for patients with fibrosis is organ transplantation; since the supply of organs is insufficient to meet the demand, patients often die while waiting to receive suitable organs. Lung fibrosis alone can be a major cause of death in scleroderma, lung disease, idiopathic pulmonary fibrosis, radiation- and chemotherapy-induced lung fibrosis and in conditions caused by occupational inhalation of dust particles.

The invention may be practiced in any subject diagnosed with, or at risk of developing, fibrosis. Fibrosis is associated with many diseases and disorders. The subject may be diagnosed with, or at risk for developing interstitial lung disease including idiopathic pulmonary fibrosis, scleroderma, radiation-induced pulmonary fibrosis, bleomycin lung, sarcoidosis, silicosis, familial pulmonary fibrosis, an autoimmune disease or any disorder wherein one or more fibroproliferative matrix molecule deposition, enhanced pathological collagen accumulation, apoptosis and alveolar septal rupture with honeycombing occurs. The subject may be identified as having fibrosis or being at risk for developing fibrosis because of exposure to asbestos, ground stone, silica and metal dust, because of the administration of a medication, such as bleomycin, busulfan, phenytoin, and nitro furantoin, which are risk factors for developing fibrosis, or because of radiation such as in patients with head & neck cancer who develop fibrosis of the salivary glands. It is also contemplated that the compositions and methods of the invention may be used in the treatment of organ fibrosis secondary to allogenic organ transplant, e.g., graft transplant fibrosis. Non-limiting examples include renal transplant fibrosis, heart transplant fibrosis, liver transplant fibrosis, etc.

In certain embodiments, the methods of the present invention are used to treat multiple fibrotic or fibrotic-related diseases or disorders with underlying causes including myocardial infarct, cirrhosis, hepatitis, etc.

The invention may be practiced in any subject diagnosed with, or at risk of developing, scleroderma. Scleroderma is a chronic autoimmune disease characterized by fibrosis (or hardening), vascular alterations, and autoantibodies. There are two major forms: limited systemic scleroderma and diffuse systemic scleroderma. The cutaneous symptoms of limited systemic scleroderma affect the hands, arms and face. Patients with this form of scleroderma frequently have one or more of the following complications: calcinosis, Raynaud's phenomenon, esophageal dysfunction, sclerodactyly), internal organ fibrosis and telangiectasias.

Diffuse systemic scleroderma is rapidly progressing and affects a large area of the skin and one or more internal organs, frequently the kidneys, esophagus, heart and/or lungs. Localized scleroderma, such as linear scleroderma and morphea, affects the skin but not the internal organs.

Scleroderma affects the small blood vessels known as arterioles, in all organs. First, the endothelial cells of the arteriole die off apoptotically, along with smooth muscle cells. These cells are replaced by collagen and other fibrous material. Inflammatory cells, particularly CD4+ helper T cells, infiltrate the arteriole, and cause further damage.

The skin manifestations of scleroderma can be painful, can impair use of the affected area (e.g., use of the hands, fingers, toes, feet, etc.) and can be disfiguring. Skin ulceration may occur, and such ulcers may be prone to infection or even gangrene. The ulcerated skin may be difficult or slow to heal. Difficulty in healing skin ulcerations may be particularly exacerbated in patients with impaired circulation, such as those with Raynaud's phenomenon. Lung involvement is the leading cause of death in scleredoma patients, which exhibits high morbidity and mortality. In certain embodiments, the compositions and methods of the present disclosure are used to treat scleroderma, for example skin symptoms of scleroderma. In certain embodiments, treating scleroderma comprises treating skin ulceration, such as digital ulcers. Administration of the C-terminal endostatin or an endostatin-derived peptide of the invention can be used to reduce the fibrotic and/or inflammatory symptoms of scleroderma in affected tissue and/or organs.

In addition to skin symptoms/manifestations, scleroderma may also affect the heart, kidney, lungs, joints, and digestive tract. In certain embodiments, treating scleroderma includes treating symptoms of the disease in any one or more of these tissues, such as by reducing fibrotic and/or inflammatory symptoms.

Lung problems are amongst the most serious complications of scleroderma and are responsible for much of the mortality associated with the disease. The two predominant lung conditions associated with scleroderma are pulmonary fibrosis and pulmonary hypertension. A patient with lung involvement may have either or both conditions. Lung fibrosis associated with scleroderma is one example of pulmonary fibrosis that can be treated using the peptides of the invention.

Scleroderma involving the lung causes scarring (pulmonary fibrosis). Such pulmonary fibrosis occurs in about 70% of scleroderma patients, although its progression is typically slow and symptoms vary widely across patients in terms of severity. For patients that do have symptoms associated with pulmonary fibrosis, the symptoms include a dry cough, shortness of breath, and reduced ability to exercise. About 16% of patients with some level of pulmonary fibrosis develop severe pulmonary fibrosis. Patients with severe pulmonary fibrosis experience significant decline in lung function and alveolitis.

In certain embodiments, the methods of the present invention include the use of the peptides of the invention to treat scleroderma, for example lung fibrosis associated with scleroderma. Administration of the peptides of the invention can be used to reduce the fibrotic symptoms of scleroderma in lung. For example, the methods can be used to improve lung function and/or to reduce the risk of death due to scleroderma. For example, the C-terminal endostatin or an endostatin-derived peptide of the invention can be used to treat scleroderma associated interstitial lung disease.

Kidney involvement is also common in scleroderma patients. Renal fibrosis associated with scleroderma is an example of renal fibrosis that can be treated by administration of a C-terminal endostatin or an endostatin-derived peptide of the invention.

In certain embodiments, the methods of the present invention are used to treat scleroderma, for example kidney fibrosis associated with scleroderma. Administration of a C-terminal endostatin or an endostatin-derived peptide of the invention of the invention can be used to reduce the fibrotic symptoms of scleroderma in kidney. For example, the methods can be used to improve kidney function, to reduce protein in the urine, to reduce hypertension, and/or to reduce the risk of renal crisis that may lead to fatal renal failure.

In one embodiment, the method comprises reducing fibrosis in a cell or subject by administering a composition comprising a C-terminal endostatin or an endostatin-derived peptide, or nucleic acid molecule encoding a C-terminal endostatin or endostatin-derived peptide, as described herein. In one embodiment the method comprises reducing or degrading extracellular matrix protein in a cell or subject by administering a composition comprising a C-terminal endostatin or an endostatin-derived peptide, or nucleic acid molecule encoding a C-terminal endostatin or endostatin-derived peptide, as described herein.

Methods for Treatment of Acute Lung Injury

One aspect of the invention provides a method of treating or preventing acute lung injury, comprising administering to a subject a composition comprising a C-terminal endostatin or an endostatin-derived peptide, or nucleic acid molecule encoding a C-terminal endostatin or endostatin-derived peptide, as described herein. In one embodiment, acute lung injury includes, but is not limited to, ARDS virus-induced acute lung injury, SARS, COVID-19, influenza-induced acute lung injury, acute lung injury due to sepsis, pneumonia, aspiration, trauma, blood transfusions, smoke, toxic gas inhalation pancreatitis, drug overdoses, burns, and other lung injury or acute respiratory distress syndromes, including ventilator-associated lung injury, manifesting with inflammation.

Acute lung injury is associated with elevated levels of IL-6 in the lung tissue, which promotes cytokine storm. Administration of the peptides of the invention can be used to reduce the cytokine-induced symptoms of acute lung injury. For example, the methods can be used to improve lung function and/or to reduce the risk of death due to acute lung injury. For example, the C-terminal endostatin or an endostatin-derived peptide of the invention can be used to treat elevated IL-6 levels in lung tissue associated with cytokine storm and lung injury. In one embodiment the method comprises reducing IL-6 levels in a cell or subject by administering a composition comprising a C-terminal endostatin or an endostatin-derived peptide, or nucleic acid molecule encoding a C-terminal endostatin or endostatin-derived peptide, as described herein.

Administration

In certain embodiments, the method comprises administering an effective amount of a composition described herein to a subject diagnosed with, suspected of having, or at risk for developing cancer, a condition associated with tumor growth, fibrosis, a fibrotic-related disease or disorder, or acute lung injury. In certain aspects, the composition is contacted to a cell or tissue where a tumor, fibrosis, or acute lung injury is present or at risk for developing. In one embodiment, the composition is administered systemically to the subject.

The composition of the invention may be administered to a patient or subject in need in a wide variety of ways. Modes of administration include oral administration, inhalation, intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

In certain embodiments, the composition of the invention is administered during surgical resection or debulking of a tumor or diseased tissue (e.g., a fibrotic tissue). For example, in subjects undergoing surgical treatment of diseased tissue or tumor, the composition may be administered to the site in order to further treat the tumor, fibrosis, acute lung injury, or a combination thereof.

In one embodiment, the method comprises administering to the subject a scaffold comprising C-terminal endostatin or an endostatin-derived peptide, or a cell modified to express C-terminal endostatin or an endostatin-derived peptide.

Subjects to which administration of the compositions and pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by inhalation, injection, ingestion, transfusion, implantation or transplantation. The compositions described herein may be administered to a patient by orally, subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

The disclosed compounds can be used to prevent, abate, minimize, control, and/or lessen tumor proliferation or metastasis in humans and animals. The disclosed compounds can also be used to slow the rate of primary tumor growth. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis or reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

In one embodiment, the invention provides a method to treat or prevent cancer growth or metastasis comprising treating the subject with a complementary therapy for the cancer, such as surgery, chemotherapy, chemotherapeutic agent, radiation therapy, or hormonal therapy or a combination thereof, prior to, concurrently with, or subsequently to the treatment with C-terminal endostatin or an endostatin-derived peptide, or nucleic acid molecule encoding a C-terminal endostatin or an endostatin-derived peptide.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozocin), cytotoxic alkylating agents (e.g., busulfan, chlorambucil, cyclophosphamide, melphalan, or ethylsulfonic acid), alkylating agents (e.g., asaley, AZQ, BCNU, busulfan, busulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolomide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantrone, amonafide, m-AMSA, anthrapyrazole derivatives, pyrazoloacridine, bisantrene HCL, daunorubicin, deoxydoxorubicin, menogaril, N,N-dibenzyl daunomycin, oxantrazole, rubidazone, VM-26 and VP-16), and synthetics (e.g., hydroxyurea, procarbazine, o,p'-DDD, dacarbazine, CCNU, BCNU, cis-diaminedichloroplatinum, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The endostatin peptides, or nucleic acid molecule encoding the endostatin peptides, of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazine, and dacarbazine. Other cytotoxic/anti-neoplastic agents are antimetabolites for tumor cells, e.g., cytosine arabinoside, fluorouracil, methotrexate, mercaptopurine, azathioprine, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan;

cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase;

peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentine; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

In certain embodiments, methods of treating fibrosis or fibrotic-related diseases or disorders include administering a C-terminal endostatin or an endostatin-derived peptide, or a nucleic acid molecule encoding a C-terminal endostatin or endostatin-derived peptide as part of a therapeutic regimen along with one or more other drugs, biologics, or therapeutic interventions appropriate for the treatment of fibrosis. In certain embodiments, the additional drug, biologic, or therapeutic intervention is appropriate for particular symptoms associated with fibrosis. By way of example, a C-terminal endostatin or an endostatin-derived peptide of the invention may be administered as part of a therapeutic regimen along with one or more immunosuppressive agents, such as methotrexate, cyclophosphamide, azathioprine, pirfenidone, nintedanib and mycophenolate mofetil. By way of further example, a C-terminal endostatin or an endostatin-derived peptide of the invention may be administered as part of a therapeutic regimen along with one or more agents designed to increase blood flow, such as blood flow to ulcerated digits (e.g., nifedipine, amlodipine, diltiazem, felodipine, or nicardipine). By way of further example, a C-terminal endostatin or an endostatin-derived peptide of the invention may be administered as part of a therapeutic regimen along with one or more agents intended to decrease fibrosis of the skin, such as d-penicillamine, colchicine, PUVA, Relaxin, and cyclosporine. By way of further example, a C-terminal endostatin or an endostatin-derived peptide of the invention may be administered as part of a therapeutic regimen along with steroids or broncho-dilators.

In certain embodiments, methods of treating acute lung injury include administering a C-terminal endostatin or an endostatin-derived peptide, or a nucleic acid molecule encoding a C-terminal endostatin or endostatin-derived peptide as part of a therapeutic regimen along with one or more other drugs, biologics, or therapeutic interventions appropriate for the treatment of acute lung injury. In certain embodiments, the additional drug, biologic, or therapeutic intervention is appropriate for particular symptoms associated with acute lung injury. Treatments for acute lung injury are limited and include prone position, ventilation, inhaled vasodilators such as epoprostenol or nitric oxide, ECMO, neuromuscular blockers to facilitate lung protective ventilation, and steroids.

The invention encompasses administration of a C-terminal endostatin or an endostatin-derived peptide, or a nucleic acid molecule encoding a C-terminal endostatin or endostatin-derived peptide, for the treatment or prevention of diseases and disorders. To practice the methods of the invention; the skilled artisan would understand, based on the disclosure provided herein, how to formulate and administer the appropriate composition of the invention to a subject. The present invention is not limited to any particular method of administration or treatment regimen.

In one embodiment, the method comprises administering to the subject a C-terminal endostatin or an endostatin-derived peptide, a scaffold comprising C-terminal endostatin or an endostatin-derived peptide, or a cell modified to express C-terminal endostatin or an endostatin-derived peptide.

Dosage and Formulation (Pharmaceutical Compositions)

The present invention envisions treating a disease or disorder, for example, cancer, fibrosis, a fibrotic-related disease or disorder, acute lung injury, and the like, in a mammal by the administration of therapeutic agent, e.g. a C-terminal endostatin or an endostatin-derived peptide, or a nucleic acid molecule encoding a C-terminal endostatin or endostatin-derived peptide.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous, intraperitoneal, inhalation and intramuscular routes, as well as by direct injection into the diseased tissue. For example, the therapeutic agent or modified cell may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In certain embodiments, the composition of the invention is administered by inhalation. In certain embodiments, the invention is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. In certain embodiments, the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator. The powdered or aerosolized formulations, when dispersed, preferably have an average particle or droplet size in the range from about 0.1 nanometers to about 2000 micrometers, and may further comprise one or more of the additional ingredients described herein.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The agents of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, oral administration or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Endostatin Peptides for the Treatment of Tumors

The ability of endostatin peptides to block tumor growth was evaluated. The peptides were biotinylated at the N-terminus and amidated at the C-terminus.

The peptides evaluated in the experiments were:

Bio96 sequence: (SEQ ID NO: 1)
Biotin-$NH_2$-ATGQASSLL-$CONH_2$,

BioE4-03 sequence: (SEQ ID NO: 2)
Biotin-$NH_2$-SYCETWRTEAPSATGQASSLLGGRLLGQSAASCHHA-$CONH_2$,
and BioE4 sequence: (SEQ ID NO: 3)
Biotin-$NH_2$-SYCETWRTEAPSATGQASSLLGGRLLGQSAASCHHAYIVLCIENSFMT-$CONH_2$.

Statistical Methods

For each of the experiments, descriptive statistics (means and standard deviations) for tumor volumes were calculated over time for each experimental group (i.e. Experiment 1: Control vs. BioE4 (FIG. 1); Experiment 2: PBS, Bio96, and BioE4-03 (FIG. 5)). Since tumor growth tends to be curvilinear, general linear mixed models (GLMMs) were created to estimate treatment-specific growth curves over time and to make comparisons between the peptide treatments and control. Separate GLMMs were constructed for each experiment, and each GLMM included random effects for each mouse, to control for the fact that the repeated volume measurements within a given mouse were correlated with one another. Tumor volume served as the dependent variable in each model, while time (in days), time, treatment, treatment x time, and treatment x time$^2$ were included as independent variables. Using these models, the estimated mean tumor volumes at specific selected time points and the mean rate of change in the tumor volumes at specific selected time points were compared. If a mouse's tumor grew too large, it was sacrificed; however, all tumor volumes measured prior to sacrifice were included in the modeling process. SAS v9.4 (SAS Institute, Cary, NC) was used for all analyses. All hypothesis tests were 2-sided, and p-values $<0.05$ were considered statistically significant.

The results of the experiments are now described

Analysis of Effect of Endostatin Peptides on Prostate Tumor Growth

Two groups of wild type C57BL6 mice from Jax Labs were injected with TRAMP C-2 mouse prostate tumor cells in the right flank. When tumors reached ~150 $mm^3$ in size, treatment was started. Treatment consisted of peptide (Bio E4) dissolved in water or water as a vehicle control given twice per week in a volume of 100 μl via oral gavage at a dose of 50 μg/dose. Tumors were measured 3 times/week.

Figure 2A:
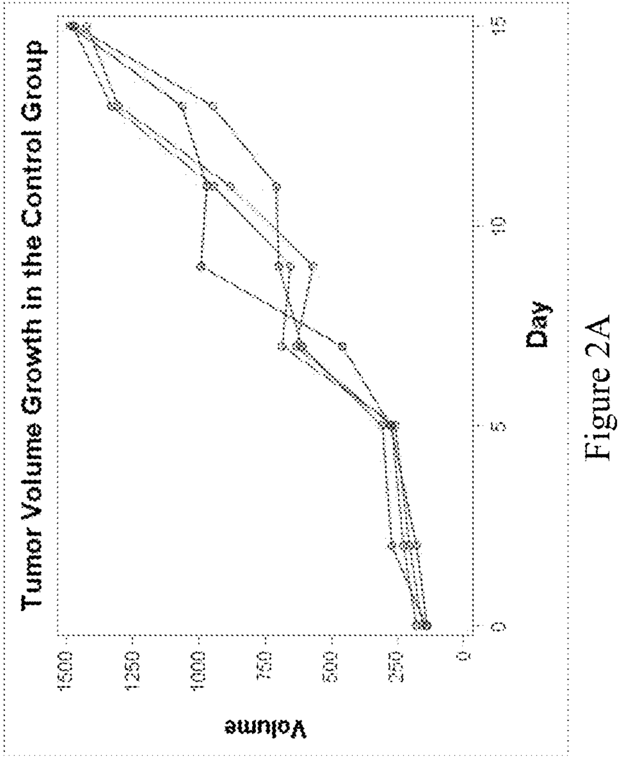

Direct comparisons were made between BioE4 and control with respect to the mean tumor volumes at Day 15 and the mean rate of change in the tumor volumes at Day 15 (FIG. 1 through FIG. 3). Model-based estimates are in FIG. 4. At day 15, the mean tumor volume was significantly (p=0.0001) greater in the Control group when compared to the BioE4 group, and the mean rate of increase in the volume on day 15 was also significantly (p=0.02) greater in the Control group when compared to the BioE4 group.

Analysis of Effect of Endostatin Peptides on Colon Adenocarcinoma Tumor Growth sMIC tolerant transgenic (MB481 strain) mice (Liu et al, Perturbation of NK cell peripheral homeostasis accelerates prostate carcinoma metastasis. J. Clin. Invest. 123:4410, 2013) were injected with $1\times10^5$ mc-38 colon adenocarcinoma tumor cells via subcutaneous injection When tumor size reached approximately 75 $mm^3$, treatment was started. start treatment at four group. Bio96 100 μg/mouse, BioE4-03 100 μg/mouse, were given via oral gavage in a volume of 100 μl. PBS (100 μl) was given as a vehicle control. Peptides and vehicle were administered twice/week. Tumor volume was measured 3 times per week.

Figure 6A:
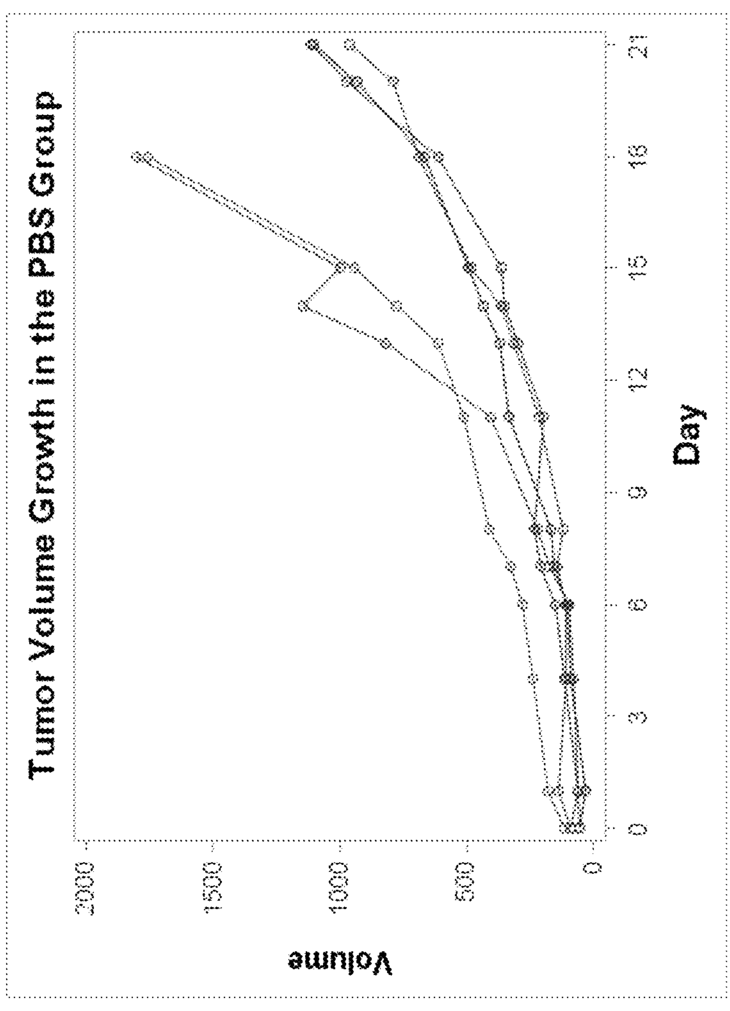
FIG. 6A, FIG. 6B and FIG. 6C depict the results of example experiments demonstrating mouse-specific tumor growth trajectories, separated for the Control, Bio96, and BioE4-03 groups.
Figure 6B:
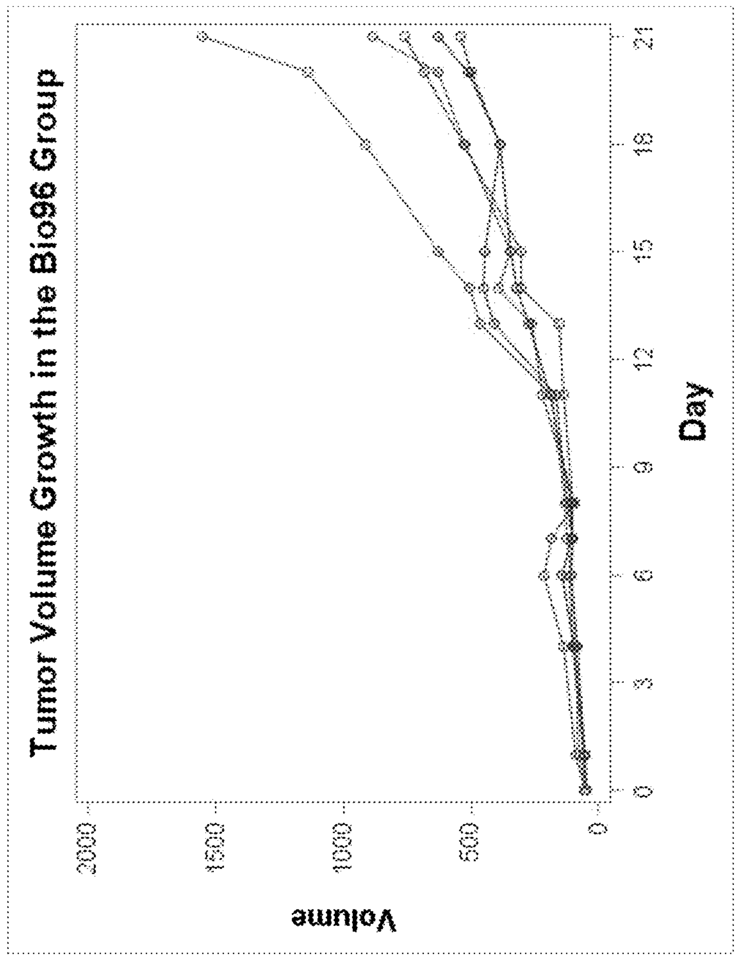
Figure 6C:
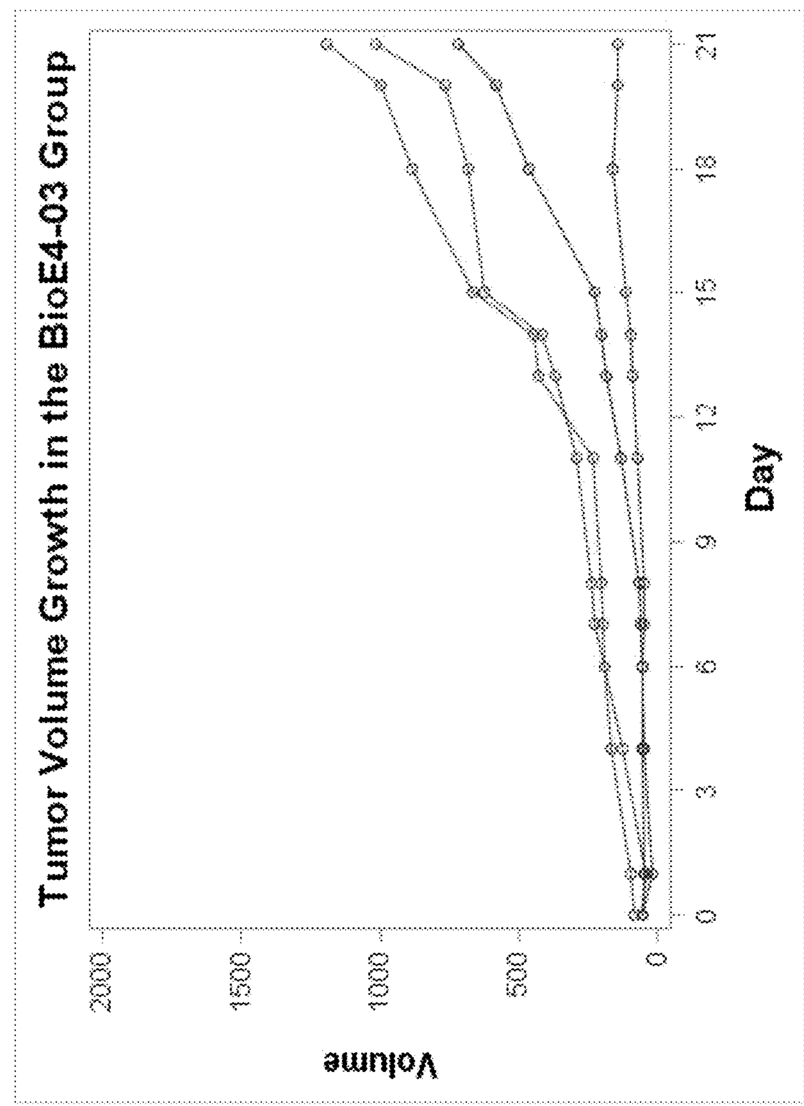

Direct comparisons were made between the PBS control and Bio96 and between PBS and BioE4-03 with respect to the mean tumor volumes at Day 21 and the mean rate of change in the tumor volumes at Day 21 (FIG. 5 through FIG. 7). Model-based estimates are shown in FIG. 8. At day 21, the mean tumor volume was significantly greater in the PBS control group when compared to the Bio96 group (1492.1 $mm^3$ vs. 871.4 $mm^3$, p=0.003), and the mean tumor volume was significantly greater in the PBS control group when compared to the BioE4-03 group (1492.1 $mm^3$ vs. 767.7 $mm^3$, p=0.0009). At day 21, the mean rate of increase in the volume was significantly greater in the PBS control group when compared to the Bio96 group (151.1 $mm^3$ per day vs. 90.6 $mm^3$ per day, p=0.004), and the mean rate of increase in the volume was significantly greater in the PBS control group when compared to the BioE4-03 group (151.1 $mm^3$ per day vs. 76.0 $mm^3$ per day, p=0.0008). Although these p-values were not adjusted for multiple comparisons, they would remain statistically significant if, for example, a Bonferroni adjustment was made.

Histologic Analysis of Tumors

Figure 9:
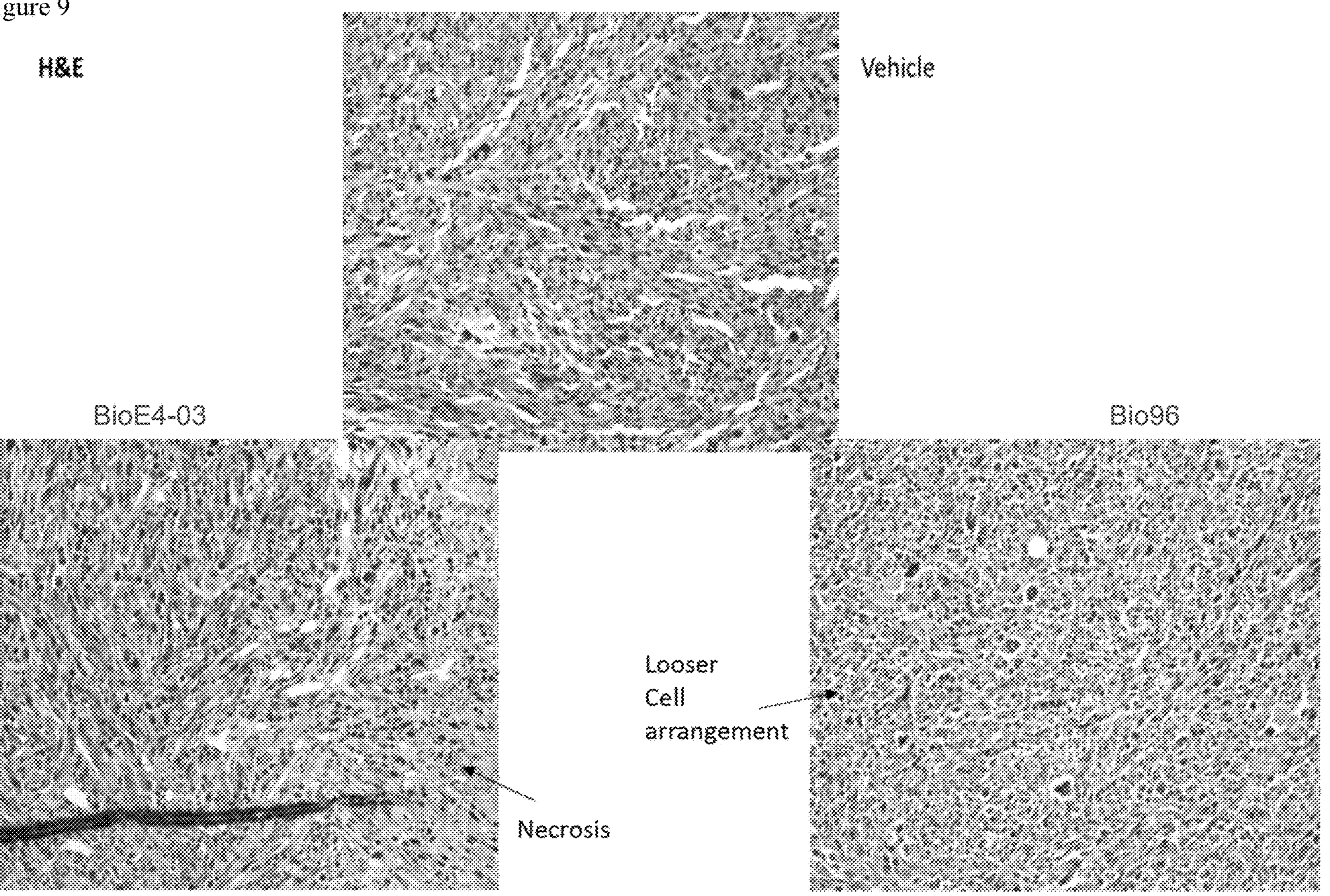
FIG. 9 depicts an exemplary histologic analysis of tumors using haematoxylin and eosin (H & E) staining.
Figure 10:
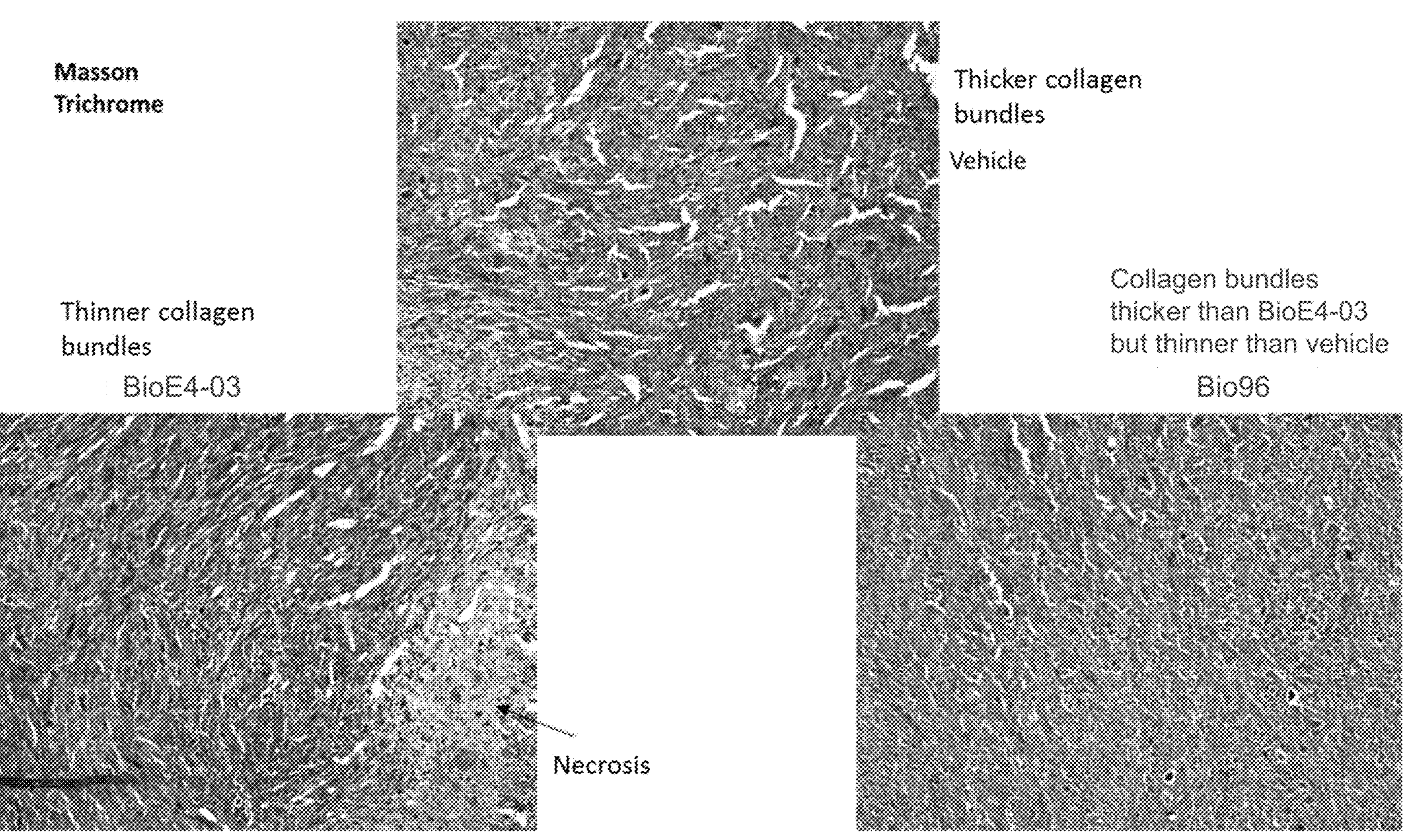
FIG. 10 depicts an exemplary histologic analysis of tumors using Masson Trichrome stain.

Histological analysis of tumors treated with vehicle alone, or with BioE4-03 or Bio96 peptides was performed. Tumors from mice treated with Bio-E4-03 had notable necrosis (H & E) (FIG. 9). Tumors from mice treated with Bio-E4-03 or Bio96 had looser cell arrangement (H & E) (FIG. 9). Tumors from mice treated with BioE4-03 or Bio96 showed thinner collagen bundles in the tumors compared to tumors from vehicle treated mice (Masson Trichrome stain) (FIG. 10).

Effects of BioE4-03 on Human Tumor Cells

In order to identify the potential mechanism by which the endostatin-derived peptides may reduce tumor growth, the effects of BioE4-03 on human tumor cells were tested.

The expression of several genes implicated in tumorigenesis, angiogenesis and cancer stem cell renewal was measured in a variety of tumor types and organs. The findings suggest that the endostatin-derived peptide E4-03 reduces tumor growth via regulation of multiple genes implicated in tumorigenesis and angiogenesis in the human cancer cells tested below.

Figure 11:
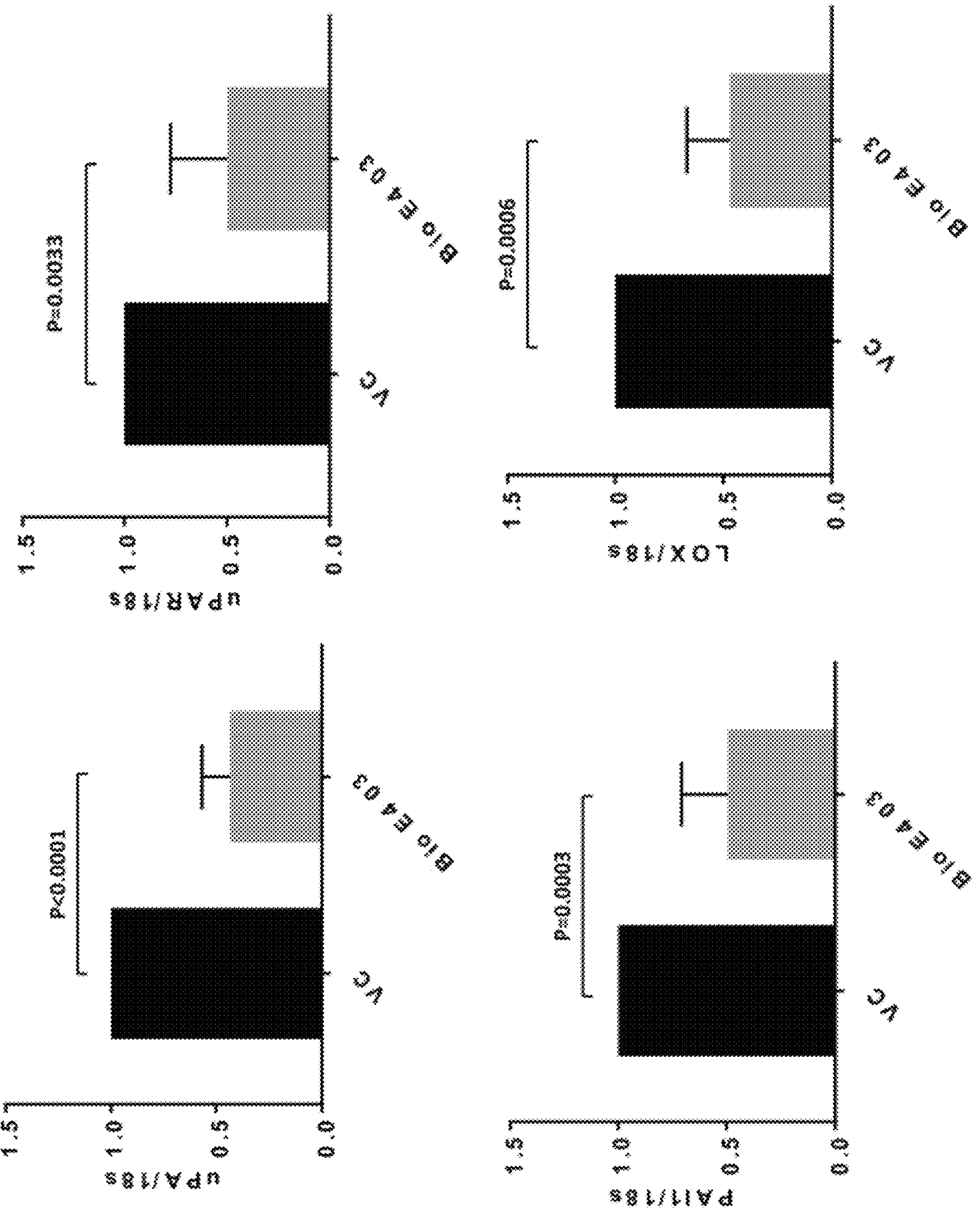
FIG. 11 depicts an exemplary analysis of gene expression in A549 cells (human lung adenocarcinoma cells.)

A549 Cells (Human Lung Adenocarcinoma Cells):

Tumor cells were treated with 10 μg/ml BioE4-03 for 48 hours. RNA was extracted and analyzed by real-time PCR. N=6-8 independent experiments. Statistical analysis was done using the paired t-test. Expression of uPA, uPAR, PAI-I, LOX, PDGF-A, VEGF-A, and IL-6 were significantly reduced by BioE4-03 (FIG. 11).

Figure 12:
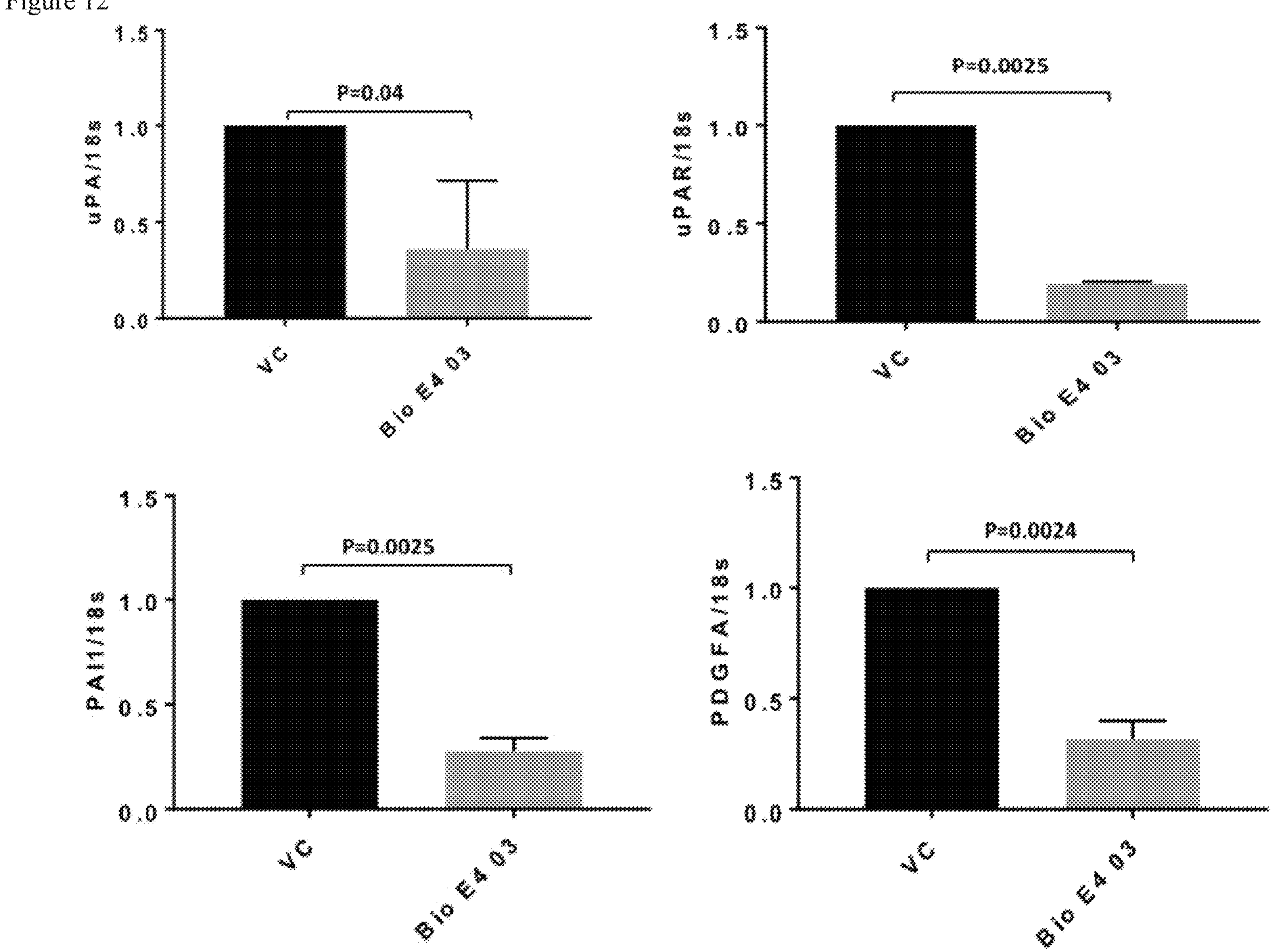
FIG. 12 depicts an exemplary analysis of gene expression in HCT116T cells (human colon carcinoma cells.)

HCT116T Cells (Human Lung Colon Carcinoma Cells):

Tumor cells were treated with 10 μg/ml BioE4-03 for 48 hours. RNA was extracted and analyzed by real-time PCR. N=3-4 independent experiments (except for uPAR where n=2). Expression of uPA, uPAR, PAI-I, PDGF-A, VEGF-A, and IL-6 were significantly reduced by BioE4-03 (FIG. 12).

Effect of Endostatin Peptide on Tumor Growth

Figure 26:
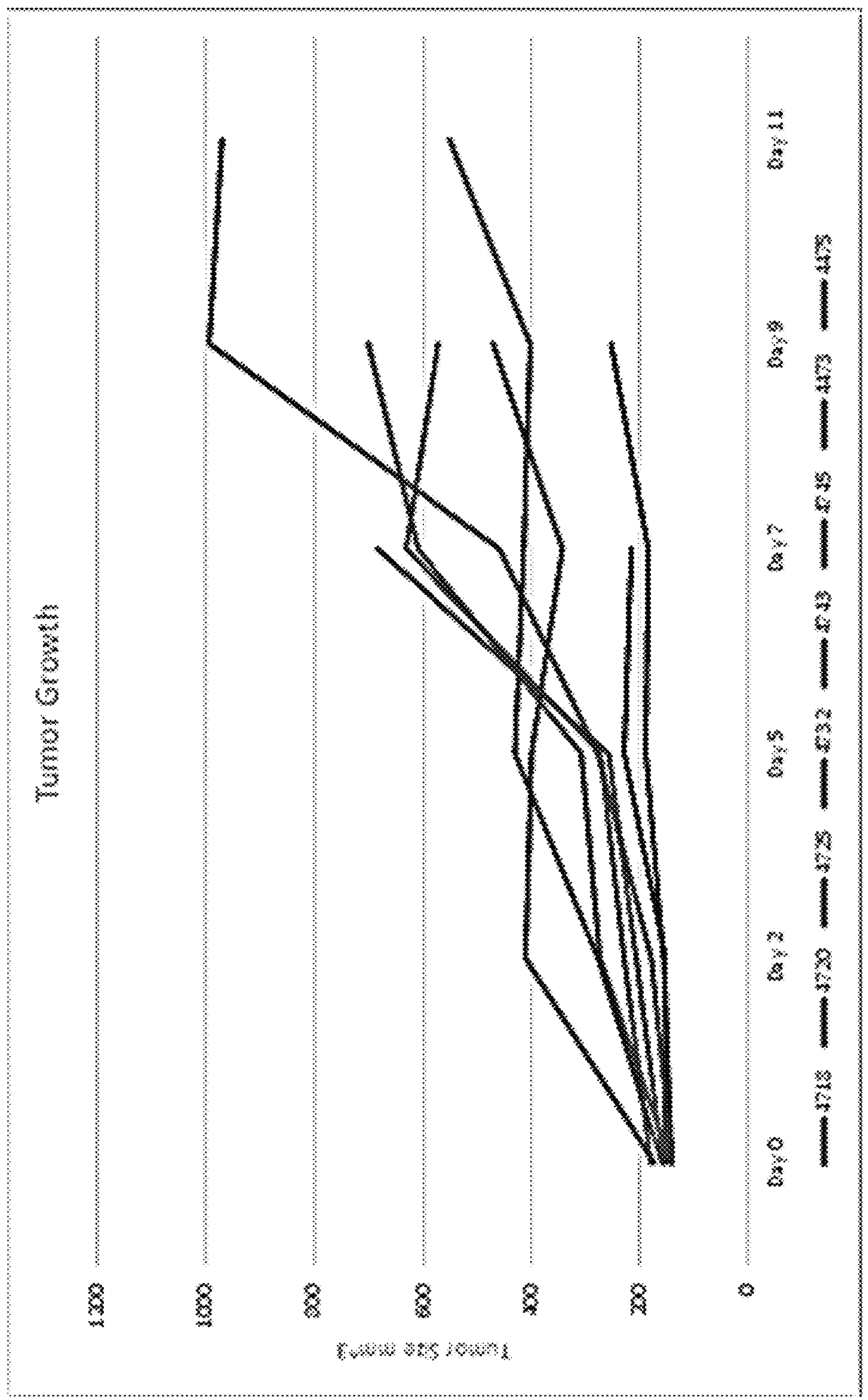
FIG. 26 depicts the effect of BioE4 given via oral gavage on tumor size in mice (Y axis). Days of treatment are shown on the X axis. Peptide was given twice per week. Red line indicates mice with untreated tumors and blue depicts mice treated with BioE4.

FIG. 26 depicts the effect of E4 given via oral gavage on tumor size in mice (Y axis). Days of treatment are shown on the X axis. Peptide was given twice per week. Red line indicates mice with untreated tumors and blue depicts mice treated with E4.

Figure 27:
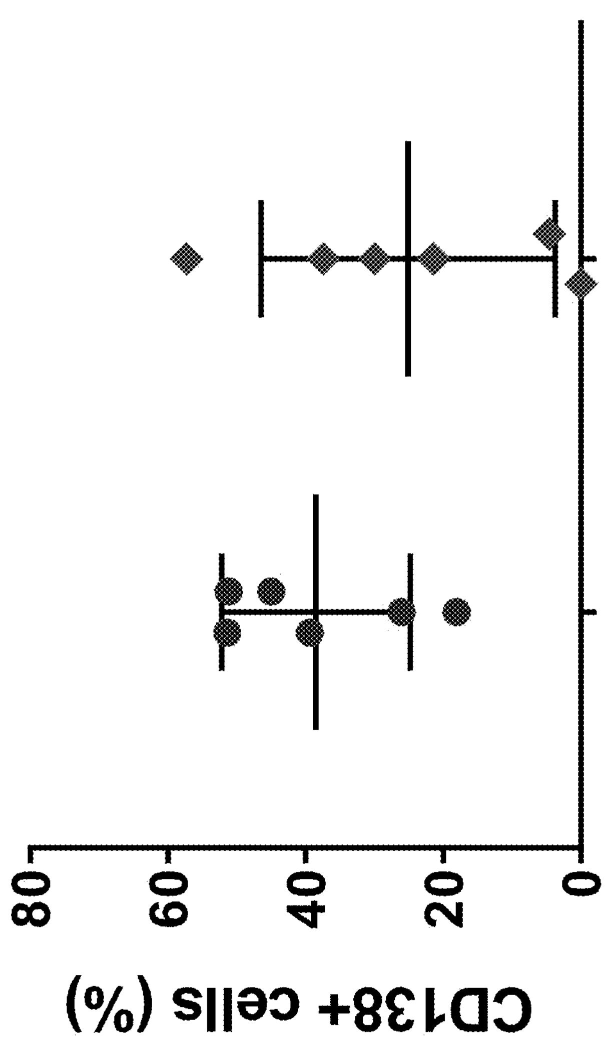
FIG. 27 depicts the effect of E4 administered orally on bone marrow infiltration of CD138+ myeloma plasma cells 49 days after injection of bortezomib resistant multiple myeloma cells (MM.1S BzR). E4 or vehicle was first administered 14 days after injection of MM.1S BzR cells and twice per week thereafter. The number of CD138+ myeloma plasma cells in the bone marrow was used as an indicator of tumor burden and efficacy of peptide.

MM.1S BzR Cells (Bortezomib Resistant Multiple Myeloma Cells):

Immunodeficient NOD-scid IL2Rgamma$^{null}$ mice were injected with $1\times10^6$ bortezomib resistant multiple myeloma cells (MM.1S BzR) via the lateral tail vein. After 14 days, treatments with BioE4 peptide given orally at 10 mg/kg twice per week were initiated. Mice were monitored daily for qualitative signs of disease progression. Bone marrow infiltration of CD138+ myeloma plasma cells was assessed at day 49 to measure the number of CD138+ myeloma plasma cells as an indicator of tumor burden and efficacy of peptide (FIG. 27).

Example 2

Endostatin Peptide Domain Testing

Variants of the Bio-E4-03 and Bio96 Endostatin peptides were evaluated for their effects on gene expression in different cells. In some experiments, the peptides were biotinylated at the N-terminus and amidated at the C-terminus.

The Peptides Evaluated in the Experiments were:

```
E4-03:
                                    (SEQ ID NO: 2)
SYCETWRTEAPSATGQASSLLGGRLLGQSAASCHHA

96-17:
                                    (SEQ ID NO: 4)
ATGQASSLLGGRLLGQSAASCHHA

96-87:
                                    (SEQ ID NO: 5)
ATGQASSLLGGRLLGQ

91-96:
                                    (SEQ ID NO: 6)
SYCETWRTEAPSATGQASSLL

91-87:
                                    (SEQ ID NO: 7)
SYCETWRTEAPSATGQASSLLGGRLLGQ
```

Gene Expression in Normal Lung Fibroblasts

Figure 13:
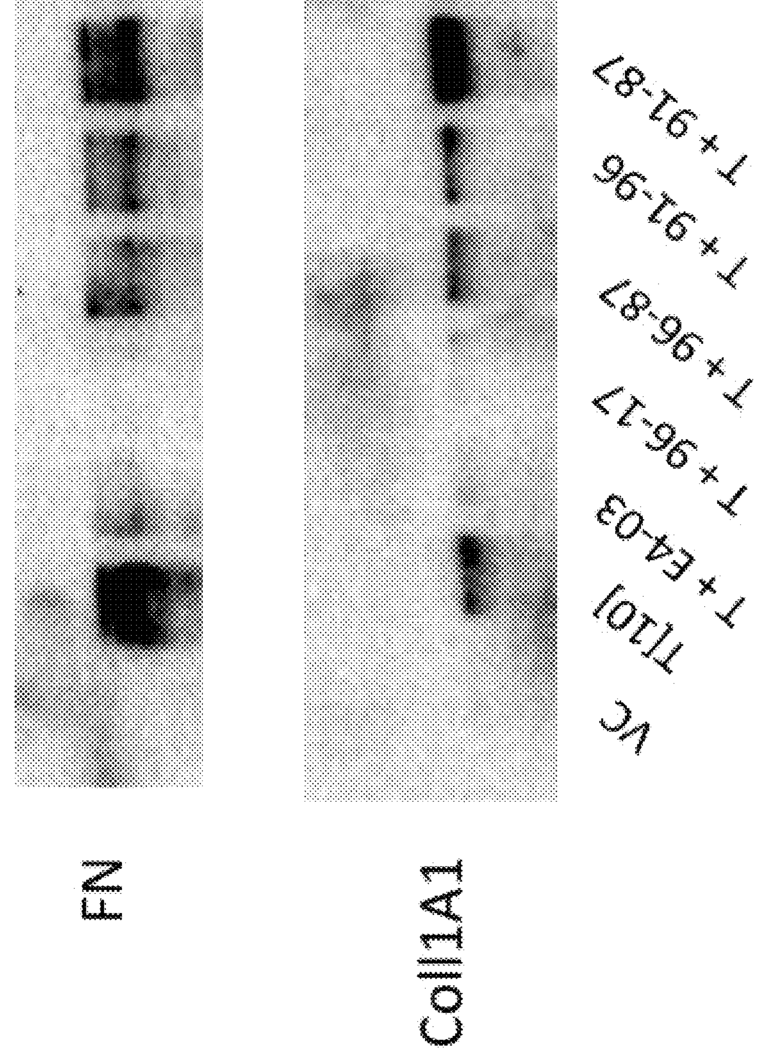
FIG. 13 depicts an exemplary analysis of protein expression in normal lung fibroblasts using different endostatin peptides.

Normal lung fibroblasts were treated with vehicle as control (VC) or TGFbeta (T) in the presence or absence of 10 μg/ml of various peptide fragments. The extracellular matrix proteins, Collagen 1A1 and fibronectin (FN) were assessed using immunoblotting. E4-03 and 96-17 were effective at reducing FN and Col1A1 levels that were induced by TGFbeta, while 96-87, 91-96 and 91-87 were not (FIG. 13).

Figure 14:
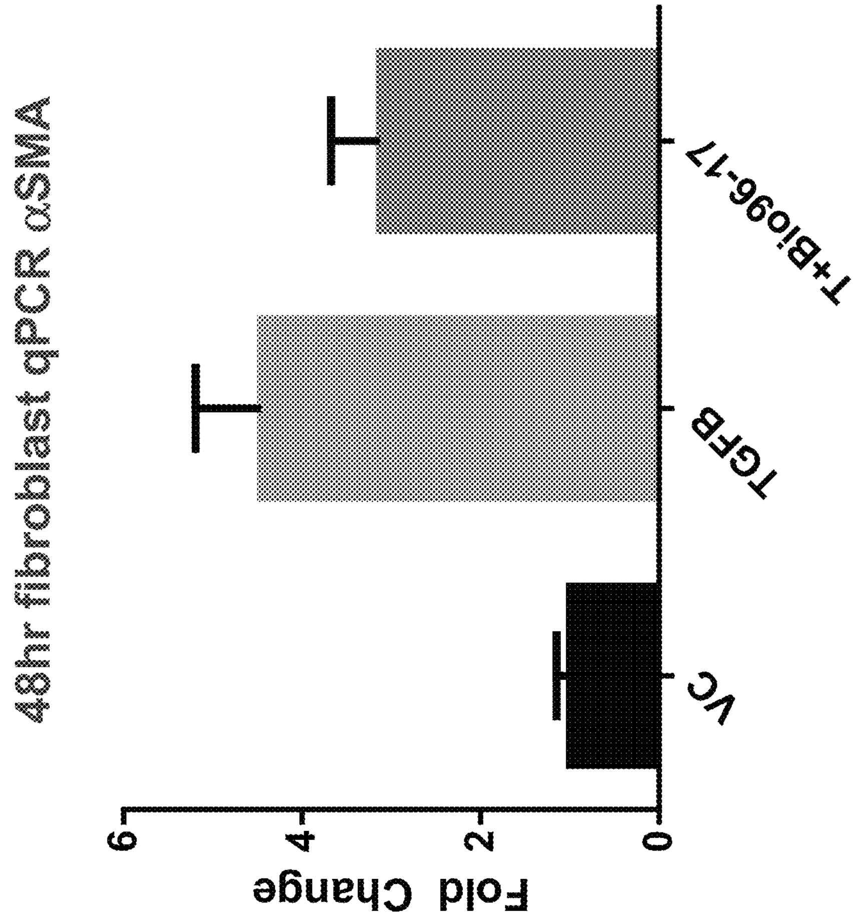
FIG. 14 depicts an exemplary analysis of gene expression in fibroblasts from lung tissues of normal donors treated with Bio96-17. Alpha smooth muscle actin RNA was measured via qRT-PCR in fibroblasts after 48 hours of treatment with TGFbeta in the presence or absence of peptide Bio96-17.

Fibroblasts were treated with TGFbeta with or without peptide Bio96-17 for 48 hours. RNA was extracted and levels of alpha smooth muscle actin (SMA) measured by qRT-PCR. Bio96-17 treatment resulted in a significant reduction in TGFbeta-induced SMA levels and thus myofibroblast differentiation in fibroblasts from lung tissues of normal donors (FIG. 14). Further, Bio96-17 results in a significant reduction in SMA and Coll1A2 levels in fibroblasts from lungs of patients with systemic sclerosis (SSc) (FIG. 15).

SSc fibroblasts were treated with 10 μg/ml BioE4-03 for 72 hours. RNA was extracted and used to measure SMA and Collagen 1A2. BioE4-03 results in a significant reduction in SMA and Coll1A2 levels in fibroblasts from lungs of patients with SSc (FIG. 16). Further, BioE4-03 results in a trend towards decrease in SMA and Coll1A2 levels in fibroblasts from lungs of patients with Idiopathic Pulmonary Fibrosis (IPF) (FIG. 17).

Figure 18:
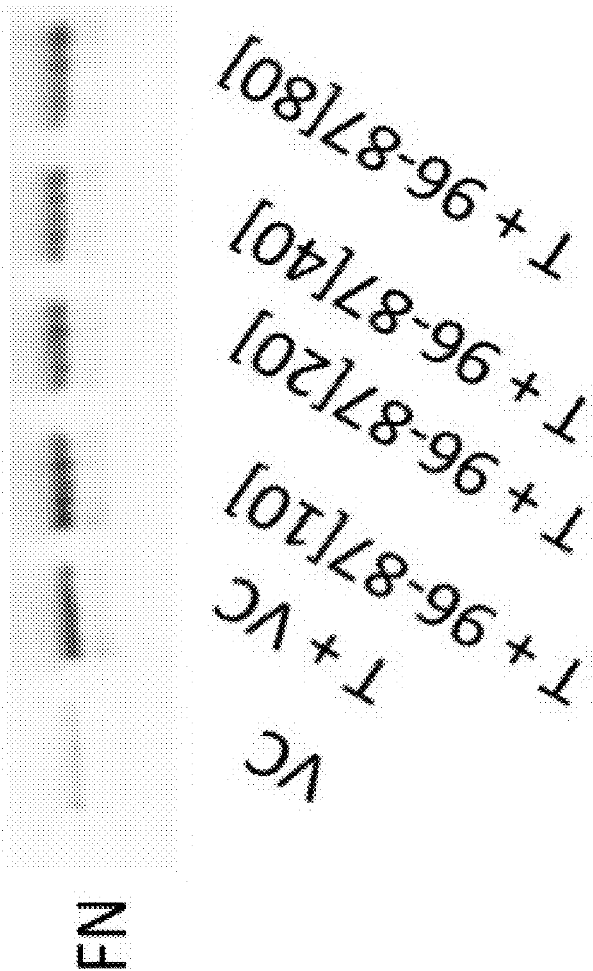
FIG. 18 depicts an exemplary analysis of protein expression in normal lung fibroblasts treated with increasing concentrations of E96-87.

Normal lung fibroblasts were treated with TGFbeta without or with increasing concentrations for 96-87. Supernatants were assessed for fibronectin levels after 72 hours of treatment. 96-87 had no effect on TGFbeta-induced FN production, even with increasing concentration from 10 μg/ml to 80 μg/ml (FIG. 18).

Ex Vivo Organ Culture Testing

Figure 19:
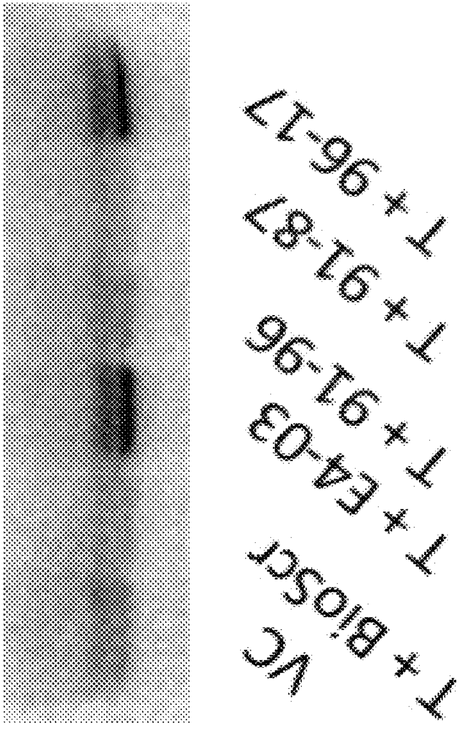
FIG. 19 depicts an exemplary analysis of matrix metalloprotease (MMP)-1 gene expression in systemic sclerosis pulmonary fibrosis lung tissues in organ culture, treated with different peptide fragments.

Systemic sclerosis pulmonary fibrosis lung tissues were divided into equal size cores. Lung tissues in organ culture were treated with different peptide fragments derived from endostatin at a final concentration of 10 μg/ml in the presence of TGFbeta for 120 hrs. The induction of matrix metalloprotease (MMP)-1 (also known as collagenase) in media conditioned by the lung tissues was examined as a measure of the ability of the peptide to reduce fibrosis and promote extracellular matrix degradation. Two of the endostatin peptide domains, E4-03 and 96-17 induced MMP-1 production, while 91-96 and 91-87 had no effect (FIG. 19).

Figure 21:
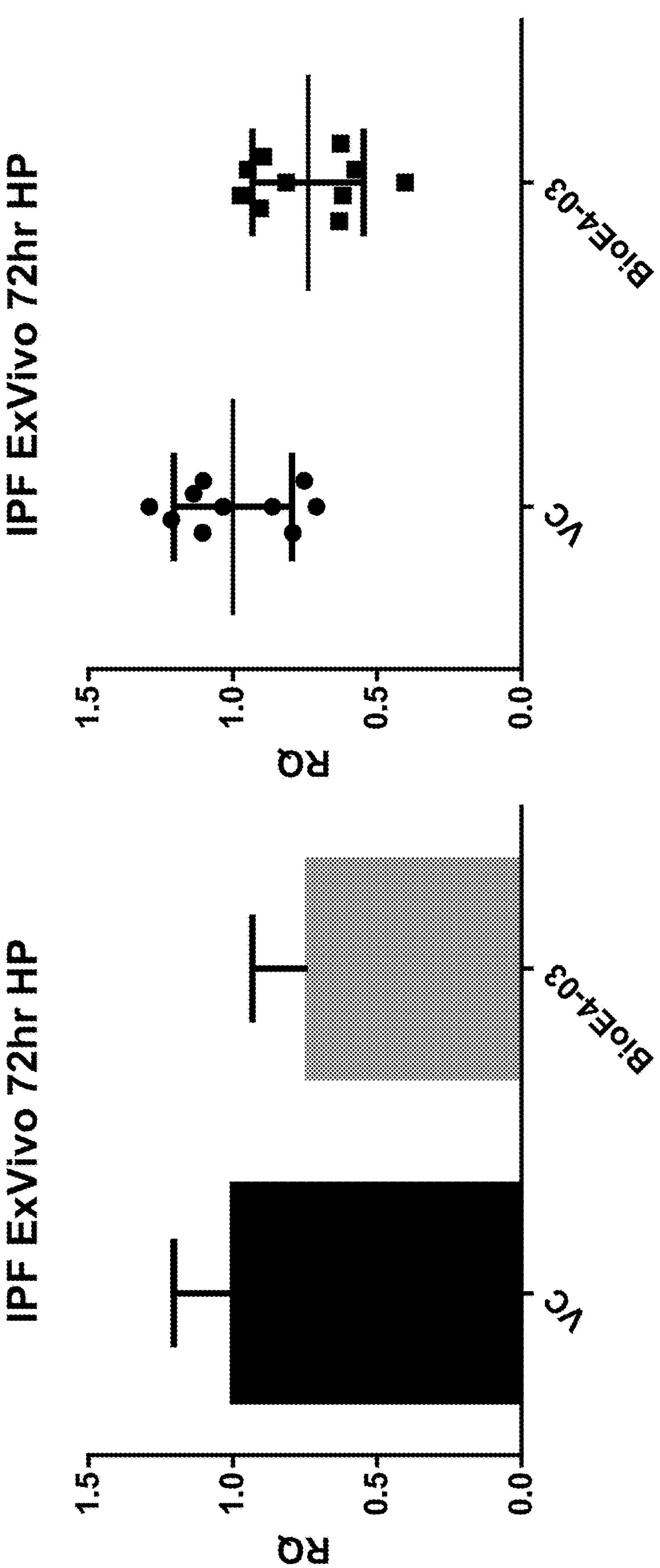
FIG. 21 depicts an exemplary analysis of hydroxyproline levels in lung tissues of patients with IPF in organ culture treated with BioE4-03.
Figure 24:
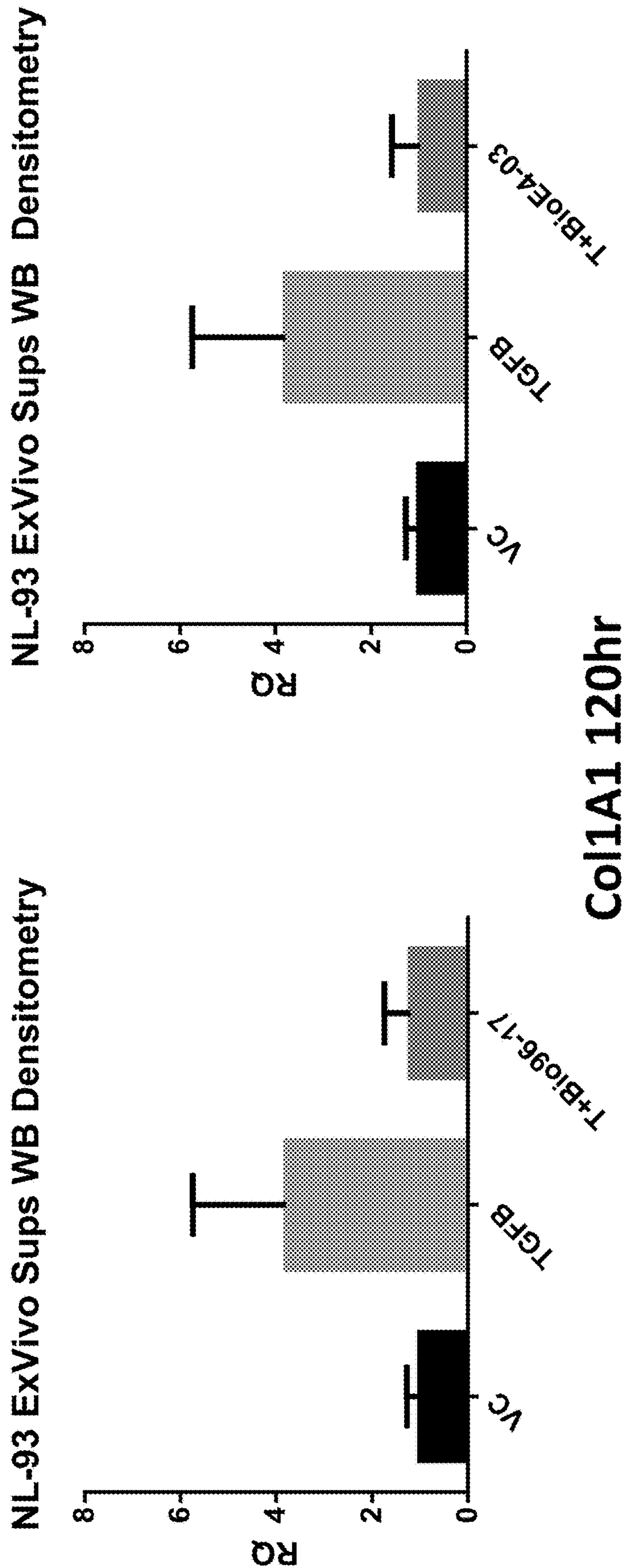
FIG. 24 depicts an exemplary analysis of the levels of secreted Col1A1 protein in lung tissues of normal donors in organ culture treated with Bio96-17, following induction of fibrosis using TGFbeta.

BioE4-03 results in a significant reduction in hydroxyproline levels in lung tissues of patients with SSc (FIG. 20) and with IPF (FIG. 21) maintained in organ culture for 72 hours. Further both BioE4-03 (FIG. 22) and Bio96-17 (FIG. 23) result in significant reductions in hydroxyproline levels in lung tissues of normal donors following induction of fibrosis using TGFbeta. Bio96-17 also results in a significant reduction in secreted Col1A1 protein levels in lung tissues of normal donors cultured for 120 hours following induction of fibrosis using TGFbeta (FIG. 24). BioE4-03 further reduces Col1A1 and fibronectin (FN) gene expression in skin tissues from donors in which fibrosis was induced with TGFbeta (FIG. 25).

Example 3

Endostatin Peptides for Treatment of Acute Lung Injury

Acute lung injury, such as ARDS and COVID-19-related lung injury, is associated with elevated levels of IL-6 in the lung tissue, which promotes cytokine storm. Therefore, there is a need for therapies that can reduce IL-6 to attenuate the cytokine-induced symptoms of acute lung injury.

Figure 28B:
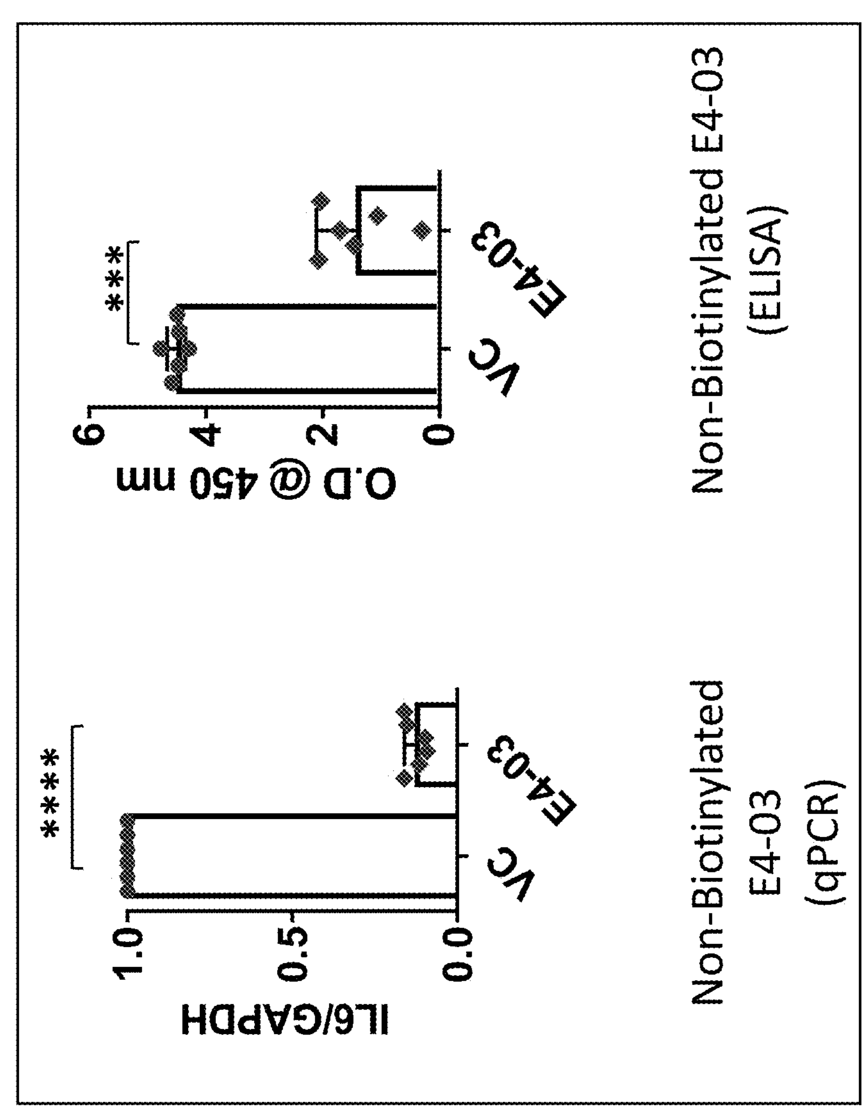
FIG. 28A and FIG. 28B depicts the results of example experiments demonstrating the effects of BioE4-03 and E4-03 on IL6.
Figure 28A:
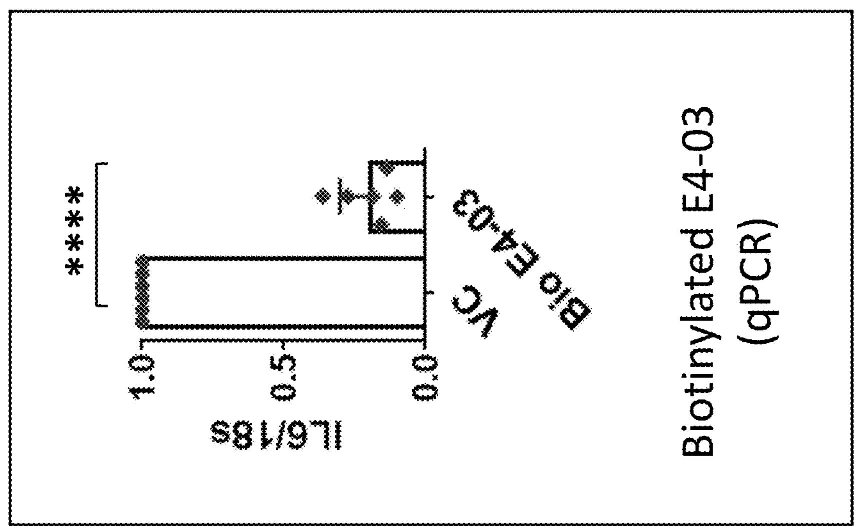

IL-6 mRNA levels were measured via qPCR in human lung adenocarcinoma cells (A549) treated for 48 hours with BioE4-03 peptide. Peptide treated cells had significantly reduced expression of IL-6 mRNA relative to vehicle controls (FIG. 28A). For comparison, a parallel experiment was done using non-biotinylated E4-03. E4-03 also reduced expression of IL-6 mRNA after 48 hours (FIG. 28B). Additionally, IL-6 protein levels in the supernatant of A549 cells were measured by ELISA after 72 hours of treatment with E4-03 peptide. IL-6 protein levels were significantly reduced in peptide treated cells relative to vehicle controls (FIG. 28B).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating cancer in a subject in need thereof, wherein the method comprises administering to the subject an effective amount of a composition comprising:

a) a C-terminal endostatin-derived peptide that is:
   i) 9 amino acids in length and has the amino acid sequence of SEQ ID NO: 1,
   ii) 36 amino acids in length and has the amino acid sequence of SEQ ID NO: 2, or
   iii) 48 amino acids in length and has the amino acid sequence of SEQ ID NO: 3; or b) a nucleic acid molecule encoding a C-terminal endostatin-derived peptide that is:
   i) 9 amino acids in length and has the amino acid sequence of SEQ ID NO: 1,
   ii) 36 amino acids in length and has the amino acid sequence of SEQ ID NO: 2, or
   iii) 48 amino acids in length and has the amino acid sequence of SEQ ID NO: 3.

2. The method of claim 1, wherein the composition comprises a C-terminal endostatin-derived peptide that is:

a) 9 amino acids in length and has the amino acid sequence of SEQ ID NO: 1, b) 36 amino acids in length and has the amino acid sequence of SEQ ID NO: 2, or c) 48 amino acids in length and has the amino acid sequence of SEQ ID NO: 3.

3. The method of claim 1, wherein the C-terminal endostatin-derived peptide is biotinylated at the N-terminus, amidated at the C-terminus, or a combination thereof.

4. The method of claim 1, wherein the cancer is selected from the group consisting of a prostate cancer, lung cancer, breast cancer, liver cancer, ovarian cancer, endometrial cancer, bladder cancer, colon cancer, lymphoma, skin cancer, pancreatic cancer, gastric cancer, myeloma, and glioma.

5. The method of claim 1, further comprising administering a second agent, wherein the second agent is an anti-cancer agent.

6. The method of claim 1, wherein the subject is a human subject.

7. The method of claim 1, wherein the subject is a cat or a dog.

8. A method of treating a fibrotic or fibrotic-related disease or disorder in a subject in need thereof, wherein the method comprises administering to the subject an effective amount of a composition comprising:

a) a C-terminal endostatin-derived peptide that is:
   i) 36 amino acids in length and has the amino acid sequence of SEQ ID NO: 2, or
   ii) 24 amino acids in length and has the amino acid sequence of SEQ ID NO: 4; or b) a nucleic acid molecule encoding a C-terminal endostatin-derived peptide that is:
   i) 36 amino acids in length and has the amino acid sequence of SEQ ID NO: 2 or
   ii) 24 amino acids in length and has the amino acid sequence of SEQ ID NO: 4.

9. The method of claim 8, wherein the fibrotic or fibrotic-related disease or disorder is selected from the group consisting of cardiac fibrosis, idiopathic pulmonary fibrosis, interstitial pulmonary fibrosis, familial pulmonary fibrosis, radiation-induced pulmonary fibrosis, Coal workers' pneumoconiosis, asbestosis, bleomycin lung, sarcoidosis, silicosis, acute lung injury, ARDS, hypertrophic scars, keloid scars, liver cirrhosis, systemic scleroderma, localized scleroderma, morphea, vascular fibrosis, kidney fibrosis, fibrosis as a result of Graft-Versus-Host Disease (GVHD), subepithelial fibrosis, endomyocardial fibrosis, uterine fibrosis, myelofibrosis, retroperitoneal fibrosis, nephrogenic systemic fibrosis, scarring after surgery, asthma, glomerulonephritis, multifocal fibrosclerosis, diabetic nephropathy, rheumatoid arthritis, atherosclerosis, radiation-induced fibrosis, chemo-therapy induced fibrosis, systemic sclerosis, hepatitis and Sjogren syndrome.

10. The method of claim 8, further comprising administering a second agent, wherein the second agent is an anti-fibrotic agent.

11. The method of claim 8, wherein the composition comprises a C-terminal endostatin-derived peptide that is:

a) 36 amino acids in length and has the amino acid sequence of SEQ ID NO: 2; or b) 24 amino acids in length and has the amino acid sequence of SEQ ID NO: 4.

12. The method of claim 11, wherein the C-terminal endostatin-derived peptide is 36 amino acids in length and has the amino acid sequence of SEQ ID NO: 2.

13. The method of claim 8, wherein the C-terminal endostatin-derived peptide is biotinylated at the N-terminus, amidated at the C-terminus, or a combination thereof.

14. The method of claim 8, wherein the subject is a human subject.

15. The method of claim 8, wherein the subject is a cat or a dog.

16. A method of treating a disease or disorder in a subject in need thereof, wherein the disease or disorder is a fibrotic or fibrotic-related disease or disorder or acute lung injury, wherein the method comprises administering to the subject an effective amount of a composition comprising:

a) a C-terminal endostatin-derived peptide that is 36 amino acids in length and has the amino acid sequence of SEQ ID NO: 2; or b) a nucleic acid molecule encoding a C-terminal endostatin-derived peptide that is 36 amino acids in length and has the amino acid sequence of SEQ ID NO: 2.

17. The method of claim 16, wherein the acute lung injury is selected from the group consisting of acute respiratory distress syndrome (ARDS), virus-induced acute lung injury, SARS, COVID-19, influenza-induced acute lung injury, acute lung injury due to sepsis, acute lung injury due to pneumonia, acute lung injury due to aspiration, acute lung injury due to trauma, acute lung injury due to blood transfusion, acute lung injury due to smoke, acute lung injury due to toxic gas inhalation, acute lung injury due to pancreatitis, acute lung injury due to drug overdose, acute lung injury due to burn, and ventilator-associated lung injury, manifesting with inflammation.

18. The method of claim 16, wherein the C-terminal endostatin-derived peptide is biotinylated at the N-terminus, amidated at the C-terminus, or a combination thereof.

* * * * *

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: C-terminal endostatin-derived peptide 96

<400> SEQUENCE: 1

Ala Thr Gly Gln Ala Ser Ser Leu Leu
1 5

<210> SEQ ID NO 2
<211> LENGTH: 36
<212> TYPE: PRT
<213> ORGANISM: Artificial Sequence
<220> FEATURE:
<223> OTHER INFORMATION: C-terminal endostatin-derived peptide E4-03

```
<400> SEQUENCE: 2

Ser Tyr Cys Glu Thr Trp Arg Thr Glu Ala Pro Ser Ala Thr Gly Gln
1               5                   10                  15

Ala Ser Ser Leu Leu Gly Gly Arg Leu Leu Gly Gln Ser Ala Ala Ser
            20                  25                  30

Cys His His Ala
        35


<210> SEQ ID NO 3
<211> LENGTH: 48
<212> TYPE: PRT
<213> ORGANISM: Artificial Sequence
<220> FEATURE:
<223> OTHER INFORMATION: C-terminal endostatin-derived peptide E4

<400> SEQUENCE: 3

Ser Tyr Cys Glu Thr Trp Arg Thr Glu Ala Pro Ser Ala Thr Gly Gln
1               5                   10                  15

Ala Ser Ser Leu Leu Gly Gly Arg Leu Leu Gly Gln Ser Ala Ala Ser
            20                  25                  30

Cys His His Ala Tyr Ile Val Leu Cys Ile Glu Asn Ser Phe Met Thr
        35                  40                  45


<210> SEQ ID NO 4
<211> LENGTH: 24
<212> TYPE: PRT
<213> ORGANISM: Artificial Sequence
<220> FEATURE:
<223> OTHER INFORMATION: C-terminal endostatin-derived peptide 96-17

<400> SEQUENCE: 4

Ala Thr Gly Gln Ala Ser Ser Leu Leu Gly Gly Arg Leu Leu Gly Gln
1               5                   10                  15

Ser Ala Ala Ser Cys His His Ala
            20


<210> SEQ ID NO 5
<211> LENGTH: 16
<212> TYPE: PRT
<213> ORGANISM: Artificial Sequence
<220> FEATURE:
<223> OTHER INFORMATION: C-terminal endostatin-derived peptide 96-87

<400> SEQUENCE: 5

Ala Thr Gly Gln Ala Ser Ser Leu Leu Gly Gly Arg Leu Leu Gly Gln
1               5                   10                  15


<210> SEQ ID NO 6
<211> LENGTH: 21
<212> TYPE: PRT
<213> ORGANISM: Artificial Sequence
<220> FEATURE:
<223> OTHER INFORMATION: C-terminal endostatin-derived peptide 91-96

<400> SEQUENCE: 6

Ser Tyr Cys Glu Thr Trp Arg Thr Glu Ala Pro Ser Ala Thr Gly Gln
1               5                   10                  15

Ala Ser Ser Leu Leu
            20


<210> SEQ ID NO 7
<211> LENGTH: 28
<212> TYPE: PRT
```

-continued

```
<213> ORGANISM: Artificial Sequence
<220> FEATURE:
<223> OTHER INFORMATION: C-terminal endostatin-derived peptide 91-97

<400> SEQUENCE: 7

Ser Tyr Cys Glu Thr Trp Arg Thr Glu Ala Pro Ser Ala Thr Gly Gln
1               5                   10                  15

Ala Ser Ser Leu Leu Gly Gly Arg Leu Leu Gly Gln
            20                  25
```